United States Patent
Guerrero-Preston et al.

(10) Patent No.: US 10,457,992 B2
(45) Date of Patent: Oct. 29, 2019

(54) HYPERMETHYLATION BIOMARKERS ASSOCIATED WITH POOR SURVIVAL OUTCOMES FOR HEAD AND NECK SQUAMOUS CELL CANCER

(71) Applicant: THE JOHNS HOPKINS UNIVERSITY, Baltimore, MD (US)

(72) Inventors: Rafael Guerrero-Preston, Baltimore, MD (US); Christina Michailidi, Baltimore, MD (US); David Sidransky, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 457 days.

(21) Appl. No.: 15/032,638

(22) PCT Filed: Oct. 29, 2014

(86) PCT No.: PCT/US2014/062883
§ 371 (c)(1),
(2) Date: Apr. 28, 2016

(87) PCT Pub. No.: WO2015/066170
PCT Pub. Date: May 7, 2015

(65) Prior Publication Data
US 2016/0251726 A1 Sep. 1, 2016

Related U.S. Application Data

(60) Provisional application No. 61/897,565, filed on Oct. 30, 2013.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/106* (2013.01); *C12Q 2600/118* (2013.01); *C12Q 2600/154* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

2004/0248171 A1  12/2004  Palmisano et al.
2008/0311570 A1  12/2008  Lai
2013/0071842 A1   3/2013  Guerrero-Preston et al.

OTHER PUBLICATIONS

Guerrero-Preston, R., et al., "Key tumor suppressor genes inactivated by "greater promoter" methylation and somatic mutations in head and neck cancer", (2014) Epigenetics, vol. 9, No. 7, pp. 1031-1046.
Norhany, S., et al., "Overexpression of PAX5 in oral carcinogenesis" (2006) Oncology Reports, vol. 16, pp. 1003-1008.
Palmisano, W., et al., "Aberrant promoter methylation of the transcription factor genes PAX5 α and β in human cancers", (2003) Cancer Research, vol. 63, pp. 4620-4625.
Z. Chen et al., Transcription factors E2A, FOXO1 and FOXP1 regulate recombination activating gene expression in cancer cells. PLoS One 6, e20475 (2011).
W. A. Palmisano et al., Aberrant promoter methylation of the transcription factor genes PAX5 alpha and beta in human cancers. Cancer Res 63, 4620 (Aug. 1, 2003).
E. M. Mandel, R. Grosschedl, Transcription control of early B cell differentiation. Curr Opin Immunol 22, 161 (Apr. 2010).
D. J. Todd, A. H. Lee, L. H. Glimcher, The endoplasmic reticulum stress response in immunity and autoimmunity. Nat Rev Immunol 8, 663 (Sep. 2008).
J. Aubin, M. Lemieux, J. Moreau, J. Lapointe, L. Jeannotte, Cooperation of Hoxa5 and Pax1 genes during formation of the pectoral girdle. Dev Biol 244, 96 (Apr. 1, 2002).
C. Mammucari et al., Integration of Notch 1 and calcineurin/NFAT signaling pathways in keratinocyte growth and differentiation control. Dev Cell 8, 665 (May 2005).
N. R. Manley M. R. Capecchi, The role of Hoxa-3 in mouse thymus and thyroid development. Development 121, 1989 (Jul. 1995).
L. Sang, J. M. Roberts, H. A. Coller, Hijacking HES1: how tumors co-opt the antidifferentiation strategies of quiescent cells. Trends Mol Med 16, 17 (Jan. 2010).
P. Mill et al., Sonic hedgehog-dependent activation of Gli2 is essential for embryonic hair follicle development. Genes Dev 17, 282 (Jan. 15, 2003).
L. Buttitta, R. Mo, C. C. Hui, C. M. Fan, Interplays of Gli2 and Gli3 and their requirement in mediating Shh-dependent sclerotome induction. Development 130, 6233 (Dec. 2003).
I. Rodrigo, R. E. Hill, R. Balling, A. Munsterberg, K. Imai, Pax1 and Pax9 activate Bapx1 to induce chondrogenic differentiation in the sclerotome. Development 130, 473 (Feb. 2003).
C. G. Mullighan et al., Genome-wide analysis of genetic alterations in acute lymphoblastic leukaemia. Nature 446, 758 (Apr. 12, 2007).
A. Lagergren, et al., Neuroblastoma and pre-B lymphoma cells share expression of key transcription factors but display tissue restricted target gene expression. BMC Cancer 4, 80 (Nov. 15, 2004).

(Continued)

*Primary Examiner* — Jehanne S Sitton
(74) *Attorney, Agent, or Firm* — John Hopkins Technology Ventures

(57) ABSTRACT

In accordance with one or more embodiments, the inventors have conducted the first comprehensive integrated genomic and epigenomic analysis in HNSCC, focusing on identifying genes that have concurrent promoter methylation, mutation and expression downregulation. The intersection of unbiased genome-wide methylation sequencing and methylation array screens uncovered 316 genes, which undergo promoter methylation in HNSCC. Close to 60% concordance was found between concurrent greater promoter methylation and gene downregulation, with PAX1 and PAX5 exhibiting the greatest expression loss. Methods for analyzing tissue samples from a subject for increased risk of poor survival outcomes from HNSCC are provided. Kits for measuring promoter methylation of the genes are also provided.

6 Claims, 15 Drawing Sheets

Specification includes a Sequence Listing.

(56) References Cited

OTHER PUBLICATIONS

M. O. Hoque et al., Quantitation of promoter methylation of multiple genes in urine DNA and bladder cancer detection. Journal of the National Cancer Institute 98, 996 (Jul. 19, 2006).

B. Benassi et al., MYC is activated by USP2a-mediated modulation of microRNAs in prostate cancer. Cancer Discov 2, 236 (Mar. 2012).

A. E. Ross et al., Gene expression pathways of high grade localized prostate cancer. Prostate, (Feb. 25, 2011).

N. Agrawal et al., Exome sequencing of head and neck squamous cell carcinoma reveals inactivating mutations in NOTCH1. Science 333, 1154 (Aug. 26, 2011).

N. Stransky et al., The mutational landscape of head and neck squamous cell carcinoma. Science 333, 1157 (Aug. 26, 2011).

M. L. Poeta et al., TP53 mutations and survival in squamous-cell carcinoma of the head and neck. N Engl J Med 357, 2552 (Dec. 20, 2007).

K. K. Ang et al., Human papillomavirus and survival of patients with oropharyngeal cancer. N Engl J Med 363, 24 (Jul. 1, 2010).

R. Guerrero-Preston et al., NID2 and HOXA9 promoter hypermethylation as biomarkers for prevention and early detection in oral cavity squamous cell carcinoma tissues and saliva. Cancer prevention research 4, 1061 (Jul. 2011).

A. L. Carvalho et al., Deleted in colorectal cancer is a putative conditional tumorsuppressor gene inactivated by promoter hypermethylation in head and neck squamous cell carcinoma. Cancer Res 66, 9401 (Oct. 1, 2006).

S. Demokan et al., KIF1A and EDNRB are differentially methylated in primary HNSCC and salivary rinses. Int J Cancer 127, 2351 (Nov. 15, 2010).

C. R. Leemans, et al., The molecular biology of head and neck cancer. Nature reviews. Cancer 11, 9 (Jan. 2011).

L. G. Morris et al., Recurrent somatic mutation of FAT1 in multiple human cancers leads to aberrant Wnt activation. Nat Genet 45, 253 (Mar. 2013).

R. L. Riley, et al., Deficient B lymphopoiesis in murine senescence: potential roles for dysregulation of E2A, Pax-5, and STAT5. Semin Immunol 17, 330 (Oct. 2005).

S. Mani et al., DNA methylation changes associated with risk factors in tumors of the upper aerodigestive tract. Epigenetics: official journal of the DNA Methylation Society 7, 270 (Mar. 2012).

R. A. Irizarry et al., The human colon cancer methylome shows similar hypo- and hypermethylation at conserved tissue-specific CpG island shores. Nat Genet 41, 178 (Feb. 2009).

E. Mena et al., 11C-Acetate PET/CT in localized prostate cancer: a study with MRI and histopathologic correlation. Journal of nuclear medicine : official publication, Society of Nuclear Medicine 53, 538 (Apr. 2012).

E. T. Stuart, et al., Loss of p53 function through PAX mediated transcriptional repression. EMBO J 14, 5638 (Nov. 15, 1995).

P. O'Brien, et al., The Pax-5 gene: a pluripotent regulator of B-cell differentiation and cancer disease. Cancer Res 71, 7345 (Dec. 15, 2011).

C. B. Moelans, et al., Frequent promoter hypermethylation of BRCA2, CDH13, MSH6, PAX5, PAX6 and WT1 in ductal carcinoma in situ and invasive breast cancer. J Pathol 225, 222 (Oct. 2011).

E. Torlakovic et al., Pax-5 expression in nonhematopoietic tissues. Am J Clin Pathol 126, 798 (Nov. 2006).

W. Liu et al., Paired box gene 5 is a novel tumor suppressor in hepatocellular carcinoma through interaction with p53 signaling pathway. Hepatology 53, 843 (Mar. 2011).

X. Li et al., Epigenetic inactivation of paired box gene 5, a novel tumor suppressor gene, through direct upregulation of p53 is associated with prognosis in gastric cancer patients. Oncogene 31, 3419 (Jul. 19, 2012).

K. P. Nera et al., Loss of Pax5 promotes plasma cell differentiation. Immunity 24, 283 (Mar. 2006).

C. Cobaleda, et al., Pax5: the guardian of B cell identity and function. Nat Immunol 8, 463 (May 2007).

V. Bolos, et al., Notch signaling in development and cancer. Endocr Rev 28, 339 (May 2007).

A. Sengupta et al., Deregulation and cross talk among Sonic hedgehog, Wnt, Hox and Notch signaling in chronic myeloid leukemia progression. Leukemia 21, 949 (May 2007).

D. S. Wall et al., Progenitor cell proliferation in the retina is dependent on Notch independent Sonic hedgehog/Hes1 activity. J Cell Biol 184, 101 (Jan. 12, 2009).

L. Landsman, et al., Elevated Hedgehog/Gli signaling causes beta-cell dedifferentiation in mice. Proc Natl Acad Sci U S A 108, 17010 (Oct. 11, 2011).

C. Cillo, et al., Homeobox genes in normal and malignant cells. J Cell Physiol 188, 161 (Aug. 2001).

M. Schubert et al., Retinoic acid signaling acts via Hox1 to establish the posterior limit of the pharynx in the chordate amphioxus. Development 132, 61 (Jan. 2005).

D. Koop et al., Retinoic acid signaling targets Hox genes during the amphioxus gastrula stage: insights into early anterior-posterior patterning of the chordate body plan. Dev Biol 338, 98 (Feb. 1, 2010).

W. M. Koch et al., p53 mutation and locoregional treatment failure in head and neck squamous cell carcinoma. Journal of the National Cancer Institute 88, 1580 (Nov. 6, 1996).

R. A. Harris et al., Comparison of sequencing-based methods to profile DNA methylation and identification of monoallelic epigenetic modifications. Nature biotechnology 28, 1097 (Oct. 2010).

C. Bock et al., Quantitative comparison of genome-wide DNA methylation mapping technologies. Nature biotechnology 28, 1106 (Oct. 2010).

S. Yegnasubramanian et al., Chromosome-wide mapping of DNA methylation patterns in normal and malignant prostate cells reveals pervasive methylation of gene-associated and conserved intergenic sequences. BMC genomics 12, 313 (2011).

Y. Zhang et al., Model-based analysis of ChIP-Seq (MACS). Genome Biol 9, R137 (2008).

J. Feng, et al., Identifying ChIP-seq enrichment using MACS. Nature protocols 7, 1728 (Sep. 2012).

R. Jaenisch, et al., Epigenetic regulation of gene expression: how the genome integrates intrinsic and environmental signals. Nat Genet 33 Suppl, 245 (Mar. 2003).

K. D. Hansen et al., Increased methylation variation in epigenetic domains across cancer types. Nat Genet 43, 768 (Aug. 2011).

J. T. Leek, et al., The sva package for removing batch effects and other unwanted variation in high throughput experiments. Bioinformatics 28, 882 (Mar. 15, 2012).

F. Marabita et al., An evaluation of analysis pipelines for DNA methylation profiling using the Illumina HumanMethylation450 BeadChip platform. Epigenetics : official journal of the DNA Methylation Society 8, 333 (Mar. 1, 2013).

S. Y. Kim, et al., PAGE: parametric analysis of gene set enrichment. BMC bioinformatics 6, 144 (2005).

S. Tyekucheva, et al., Integrating diverse genomic data using gene sets. Genome Biol 12, R105 (2011).

V. K. Mootha et al., Identification of a gene causing human cytochrome c oxidase deficiency by integrative genomics. Proc Natl Acad Sci U S A 100, 605 (Jan. 21, 2003).

A. Subramanian et al., Gene set enrichment analysis: a knowledge-based approach for interpreting genome-wide expression profiles. Proc Natl Acad Sci U S A 102, 15545 (Oct. 25, 2005).

E. M. Schaeffer et al., Androgen-induced programs for prostate epithelial growth and invasion arise in embryogenesis and are reactivated in cancer. Oncogene 27, 7180 (Dec. 4, 2008).

V. C. Daniel et al., A primary xenograft model of small-cell lung cancer reveals irreversible changes in gene expression imposed by culture in vitro. Cancer Res 69, 3364 (Apr. 15, 2009).

| SAMPLE | SITE | TOBACCO | HPV | STAGE | MF | PAX5 | PAX1 | CDKN2A | PLCB1 | SLCO4C1 | HOXC6 | TP53 |
|---|---|---|---|---|---|---|---|---|---|---|---|---|
| HN9 | OC | Y | NA | T3 | 397 | ▨ | ▨ | ▨ | | ▨ | ▨ | ▨ |
| HN19 | OP | N | + | T2 | 241 | ▨ | | ▨ | | | | |
| HN20 | OP | Y | + | T2 | 365 | ▨ | | | ▨ | ▨ | ▨ | |
| HN22 | L | Y | NA | T4 | 284 | | ▨ | | | | ▨ | ▨ |
| HN27 | OC | Y | NA | T1 | 500 | ▨ | ▨ | | ▨ | ▨ | ▨ | |
| HN32 | L | Y | NA | T3 | 396 | ▨ | ▨ | ▨ | | | | ▨ |
| HN33 | OC | N | NA | T3 | 392 | | ▨ | | | | | ▨ |
| HN35 | OC | Y | NA | T2 | 368 | ▨ | | | | | | ▨ |
| HN41 | OP | Y | + | T2 | 464 | | | | ▨ | | | |
| HN42 | OP | N | + | T2 | 358 | | | ▨ | ▨ | ▨ | | |

MF: METHYLATION FREQUENCY
METH: METHYLATION
MUT: MUTATION

METH+MUT  METH  MUT

SEQUENCE LISTING

```
<160> NUMBER OF SEQ ID NOS: 18

<210> SEQ ID NO 1
<211> LENGTH: 21
<212> TYPE: DNA
<213> ORGANISM: artificial sequence
<220> FEATURE:
<223> OTHER INFORMATION: synthetic sequence

<400> SEQUENCE: 1
gtcgatttgg gtttggtttg t                                             21

<210> SEQ ID NO 2
<211> LENGTH: 24
<212> TYPE: DNA
<213> ORGANISM: artificial sequence
<220> FEATURE:
<223> OTHER INFORMATION: synthetic sequence

<400> SEQUENCE: 2
atttcgcgta tacgcgtttg tgtt                                          24

<210> SEQ ID NO 3
<211> LENGTH: 19
<212> TYPE: DNA
<213> ORGANISM: artificial sequence
<220> FEATURE:
```

<223> OTHER INFORMATION: synthetic sequence

<400> SEQUENCE: 3
aaactcatcc tcgccgaaa                                                    19

<210> SEQ ID NO 4
<211> LENGTH: 23
<212> TYPE: DNA
<213> ORGANISM: artificial sequence
<220> FEATURE:
<223> OTHER INFORMATION: synthetic sequence

<400> SEQUENCE: 4
tcgttaggga gaaaggaatt tgt                                               23

<210> SEQ ID NO 5
<211> LENGTH: 20
<212> TYPE: DNA
<213> ORGANISM: artificial sequence
<220> FEATURE:
<223> OTHER INFORMATION: synthetic sequence

<400> SEQUENCE: 5
tttcgtcggt cgcgtttggg                                                   20

<210> SEQ ID NO 6
<211> LENGTH: 19
<212> TYPE: DNA
<213> ORGANISM: artificial sequence
<220> FEATURE:
<223> OTHER INFORMATION: synthetic sequence

<400> SEQUENCE: 6
taaatccgac gccctccta                                                    19

<210> SEQ ID NO 7
<211> LENGTH: 21
<212> TYPE: DNA
<213> ORGANISM: artificial sequence
<220> FEATURE:
<223> OTHER INFORMATION: synthetic sequence

<400> SEQUENCE: 7
gatgtgttga atggtgcgtt t                                                 21

<210> SEQ ID NO 8
<211> LENGTH: 25
<212> TYPE: DNA
<213> ORGANISM: artificial sequence
<220> FEATURE:
<223> OTHER INFORMATION: synthetic sequence

<400> SEQUENCE: 8
cggaggagta gaattcgtcg cgatt                                             25

<210> SEQ ID NO 9
<211> LENGTH: 21
<212> TYPE: DNA
<213> ORGANISM: artificial sequence
<220> FEATURE:
<223> OTHER INFORMATION: synthetic sequence

<400> SEQUENCE: 9
cgaaccgatc aaccgaaact a                                                 21

```
<210> SEQ ID NO 10
<211> LENGTH: 21
<212> TYPE: DNA
<213> ORGANISM: artificial sequence
<220> FEATURE:
<223> OTHER INFORMATION: synthetic sequence

<400> SEQUENCE: 10
ggtttaggag gaagggtatt c                                              21

<210> SEQ ID NO 11
<211> LENGTH: 24
<212> TYPE: DNA
<213> ORGANISM: artificial sequence
<220> FEATURE:
<223> OTHER INFORMATION: synthetic sequence

<400> SEQUENCE: 11
tttagtcggt cgtcgtattg gttt                                           24

<210> SEQ ID NO 12
<211> LENGTH: 20
<212> TYPE: DNA
<213> ORGANISM: artificial sequence
<220> FEATURE:
<223> OTHER INFORMATION: synthetic sequence

<400> SEQUENCE: 12
aaactacgaa ccctacgaaa                                                20

<210> SEQ ID NO 13
<211> LENGTH: 22
<212> TYPE: DNA
<213> ORGANISM: artificial sequence
<220> FEATURE:
<223> OTHER INFORMATION: synthetic sequence

<400> SEQUENCE: 13
gcgtaagaga gacgaaggta ag                                             22

<210> SEQ ID NO 14
<211> LENGTH: 23
<212> TYPE: DNA
<213> ORGANISM: artificial sequence
<220> FEATURE:
<223> OTHER INFORMATION: synthetic sequence

<400> SEQUENCE: 14
agaggttcgc gtagtttcgt cgg                                            23

<210> SEQ ID NO 15
<211> LENGTH: 23
<212> TYPE: DNA
<213> ORGANISM: artificial sequence
<220> FEATURE:
<223> OTHER INFORMATION: synthetic sequence

<400> SEQUENCE: 15
atattcgcga acacctctac tac                                            23

<210> SEQ ID NO 16
<211> LENGTH: 25
<212> TYPE: DNA
<213> ORGANISM: artificial sequence
<220> FEATURE:
<223> OTHER INFORMATION: synthetic sequence
```

```
<400> SEQUENCE: 16
tggtgatgga ggaggtttag taagt                                          25

<210> SEQ ID NO 17
<211> LENGTH: 30
<212> TYPE: DNA
<213> ORGANISM: artificial sequence
<220> FEATURE:
<223> OTHER INFORMATION: synthetic sequence

<400> SEQUENCE: 17
accaccaccc aacacacaat aacaaacaca                                     30

<210> SEQ ID NO 18
<211> LENGTH: 27
<212> TYPE: DNA
<213> ORGANISM: artificial sequence
<220> FEATURE:
<223> OTHER INFORMATION: synthetic sequence

<400> SEQUENCE: 18
aaccaataaa acctactcct cccttaa                                        27
```

HYPERMETHYLATION BIOMARKERS ASSOCIATED WITH POOR SURVIVAL OUTCOMES FOR HEAD AND NECK SQUAMOUS CELL CANCER

CROSS-REFERENCE TO RELATED APPLICATIONS

This application is a 35 U.S.C. § 371 U.S. national entry of International Application PCT/US2014/062883, having an international filing date of Oct. 29, 2014, which claims the benefit of U.S. Provisional Application No. 61/897,565, filed Oct. 30, 2013, the content of each of the aforementioned applications is herein incorporated by reference in their entirety.

STATEMENT OF GOVERNMENTAL INTEREST

This invention was made with government support under grant nos. CA084986, CA164092, DE019032, DE020957 CA121113 awarded by the NIH. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Oct. 30, 2013, is named P12502-01_ST25.txt and is 3,703 bytes in size.

BACKGROUND OF THE INVENTION

HNSCC is the sixth most common cancer worldwide with an approximate 50% five-year survival rate. Two groups that independently studied the genetic origins of HNSCC reported inactivating mutations in NOTCH. This was the first strong evidence of NOTCH1 mutations in solid tumors and analysis of the mutations suggested that NOTCH1 might act as a tumor suppressor gene in HNSCC. Notwithstanding this important finding, and contrary to original expectations, these detailed analyses of HNSCC did not uncover a great number of recurrent somatic mutations in novel genes. The number of known mutations and specific mutational hotspots in HNSCC tumors only partially explain their biological complexity and limit the development of novel diagnostic markers and therapeutic agents. TP53 was again identified as the most commonly mutated gene in HNSCC, and while mutant TP53 has been associated with poor survival the most important biologic consequences of this alteration have been elusive. Moreover, it was also known that overall and disease-specific survival is higher in patients with HPV-associated HNSCC tumors, and that this distinct molecular and pathologic subtype displays an average of 4 somatic mutations per tumor, while HPV negative HNSCC tumors harbor about 20.

Aberrant methylation changes of CpGs in the proximity of predicted transcription start sites (TSS) are the main cause of alterations in gene function and pathway deregulation in human cancer. We hypothesized that epigenetic events, specifically inactivation of tumor suppressor genes through promoter methylation, are more frequent events than somatic mutations in cancer, and may be driving tumorigenic initiation and progression. Promoter methylation of CDK2NA, HOXA9, NID2, EDNRB, KIF1A, and DCC have previously been identified and characterized in HNSCC. We thus surmised that these epigenetic alterations predominantly occur in genes or pathways with well-known somatic mutations and/or deletions in most HNSCC tumors, including TP53, CDK2NA, and more recently NOTCH1 (1, 2) and FAT9, as well as in recently described genes with low frequency mutations. HNSCCs also exhibit many chromosomal abnormalities, including amplifications of the 11q13 region containing the cyclin D1 gene and the 7p11 region encoding EGFR, which lead to proto oncogene activation. Uncovering the concurrent genomic and epigenomic alterations that modulate gene function and differentially impact cell-signaling pathways can lead to improvements in personalized diagnosis, treatment, and clinical management of HNSCC patients.

SUMMARY OF THE INVENTION

In accordance with an embodiment, the present invention provides a method for identifying a subject having an increased risk for a poor survival outcome having head and neck squamous cell cancer comprising: a) obtaining nucleic acid from a test sample from the subject, wherein the test sample is from a specimen selected from the group consisting of a tissue specimen, a biopsy specimen, a surgical specimen, saliva, and a cytological specimen; b) performing bisulfite modification to the nucleic acid in a); c) performing quantitative methylation specific PCR (QMSP) on bisulfite modified nucleic acid from b) using the PCR primers and probes specific for the promoter region of one or more genes of interest, wherein the one or more genes of interest are selected from the group consisting of PAX1, PAX5, ZIC4, and PLCB1, and the primers and probes are selected from the group consisting of SEQ ID NOS: 4-15; d) determining the promoter methylation level of the promoter regions of the one or more genes of interest in the nucleic acid from the test sample of the subject; e) providing a reference non-neoplastic test sample, wherein the test sample is from a specimen selected from the group consisting of a tissue specimen, a biopsy specimen, a surgical specimen, saliva, and a cytological specimen; f) comparing the level of promoter methylation of the one or more genes of interest from the test sample of the subject, to the level of promoter methylation of the one or more genes of in a reference non-neoplastic test sample; g) identifying said subject as having an increased risk of poor survival outcome having head and neck squamous cell cancer when the level of promoter methylation of the one or more genes of interest in the test sample of the subject, is increased relative to the level of promoter methylation of the one or more genes of interest in a reference non-neoplastic test sample indicating epigenetic silencing of the one or more genes of interest; and h) adjusting or modifying the planned treatment of the subject as a result of the increased risk of poor survival in the subject having head and neck squamous cell cancer.

In accordance with another embodiment, the present invention provides a kit for assessing a subject having an increased risk for a poor survival outcome having head and neck squamous cell cancer in a test sample containing head and neck squamous cells or nucleic acids from head and neck squamous cells, said kit comprising in a package: a reagent that (a) modifies methylated cytosine residues but not non-methylated cytosine residues, or that (b) modifies non-methylated cytosine residues but not methylated cytosine residues; and at least one set of oligonucleotide primers that specifically hybridizes under amplification conditions to a region of at least one gene selected from the group consisting of PAX1, PAX5, ZIC4, and PLCB1; and the primers and probes are selected from the group consisting of SEQ ID NOS: 4-15, wherein the region is within about 1 kb of said gene's transcription start site; and instructions for assessing head and neck squamous cell cancer using the reagents.

DETAILED DESCRIPTION OF THE INVENTION

In accordance with one or more embodiments, the inventors have conducted the first comprehensive integrated genomic and epigenomic analysis in HNSCC, focusing on identifying genes that have concurrent promoter methylation, mutation and expression downregulation. Recent studies in HNSCC, focused on therapeutic pathways affected by somatic mutations and copy number alterations (16-18), but have only described the clustering effects of global DNA methylation (16). The present inventors performed the first detailed genome wide analysis of the HNSCC methylome, examining expression-associated alterations with differential methylation patterns in the greater promoter of TSGs. This region encompasses the well-studied proximal promoter that harbors CpG Islands (1500 bases up and downstream from the TSS) and the distal promoter (6000 bp upstream of the TSS), which includes recently identified CpG Island Shores (19) and Shelves (20).

Figure 3A:
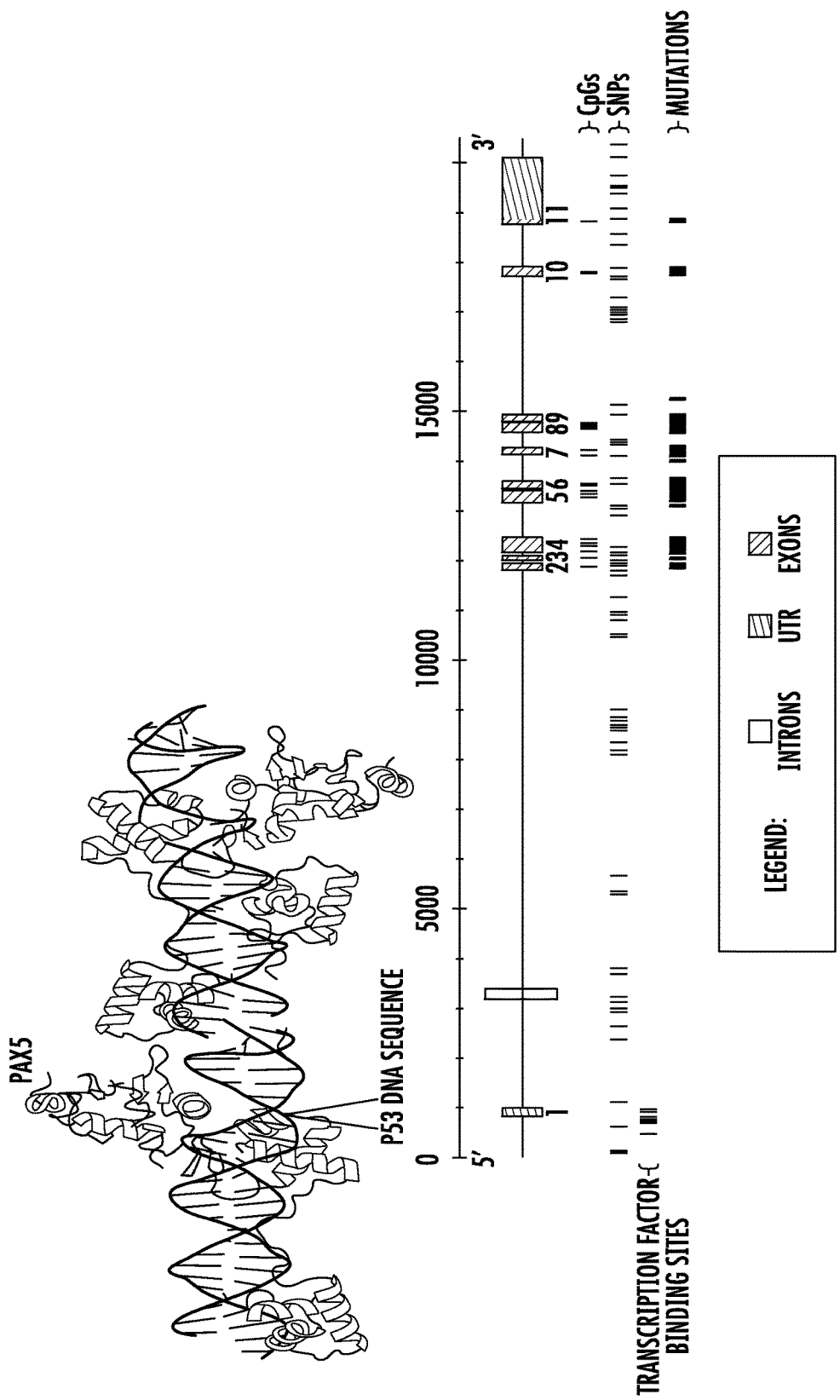
FIG. 3a is a representation of the PAX5 binding to the first exon of p53. PAX5 is represented in 3D (PDB 1K78) around the DNA. The lines converge on the p53 position in the DNA sequence.
Figure 3B:
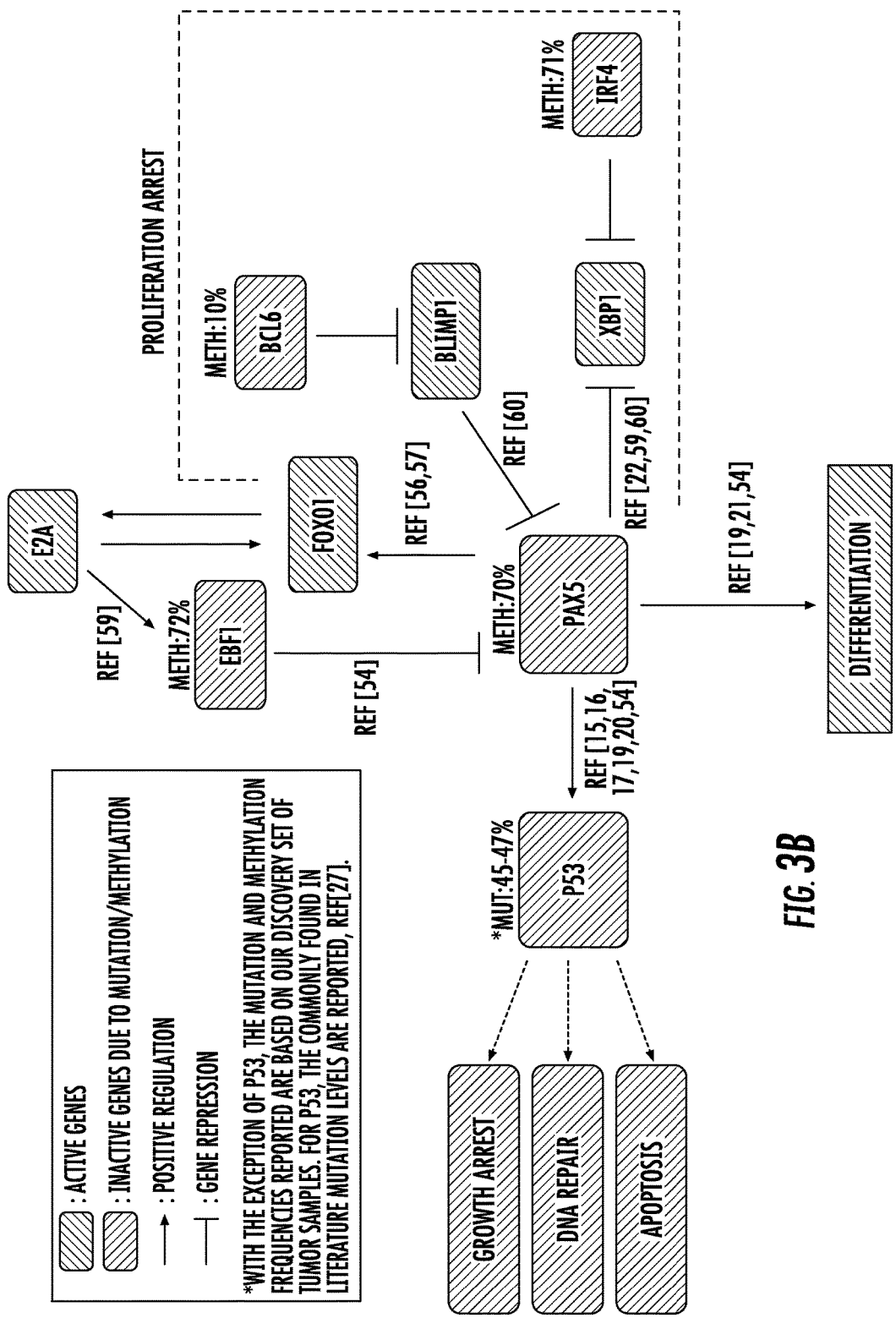
FIG. 3b is a schematic of the proposed partial pathway interplay of p53 and PAX5 in HNSCC disclosed in the present invention. Downregulation of PAX5 leads to differentiation. When methylated, PAX5 an upstream target of p53, fails to activate the latter, which is also silenced due to mutations, and thus DNA repair, apoptosis, and growth arrest pathways are inactive.

PAX5 has been reported to function as a tumor suppressor in hepatocellular carcinoma (25) and gastric cancer (26), directly binding to the p53 promoter (FIG. 3a), silencing of PAX5 due to DNA methylation has been shown to promote cell differentiation and block proliferation. In accordance with some embodiments, the present inventors now have identified a high frequency of PAX5 promoter methylation in HNSCC coinciding with low expression levels.

Agrawal et al. revealed inactivating mutations in NOTCH1 gene, depicting its importance in HNSCC proposing also a tumor suppressor function in this particular type of cancer. When NOTCH1 acts as a tumor suppressor gene it inhibits proliferation and promotes entry to differentiation (29).

The inventors have developed a set of biomarkers that can be used alone or in combinations to assess the increased risk of poor outcome from head and neck squamous cell carcinoma, an in particular oral squamous cell carcinoma. While the inventors do not intend to be bound by any theories of mechanism of action, the biomarkers which are hypermethylated and hypoexpressed in cancer cells, may be tumor suppressors.

Figure 9:
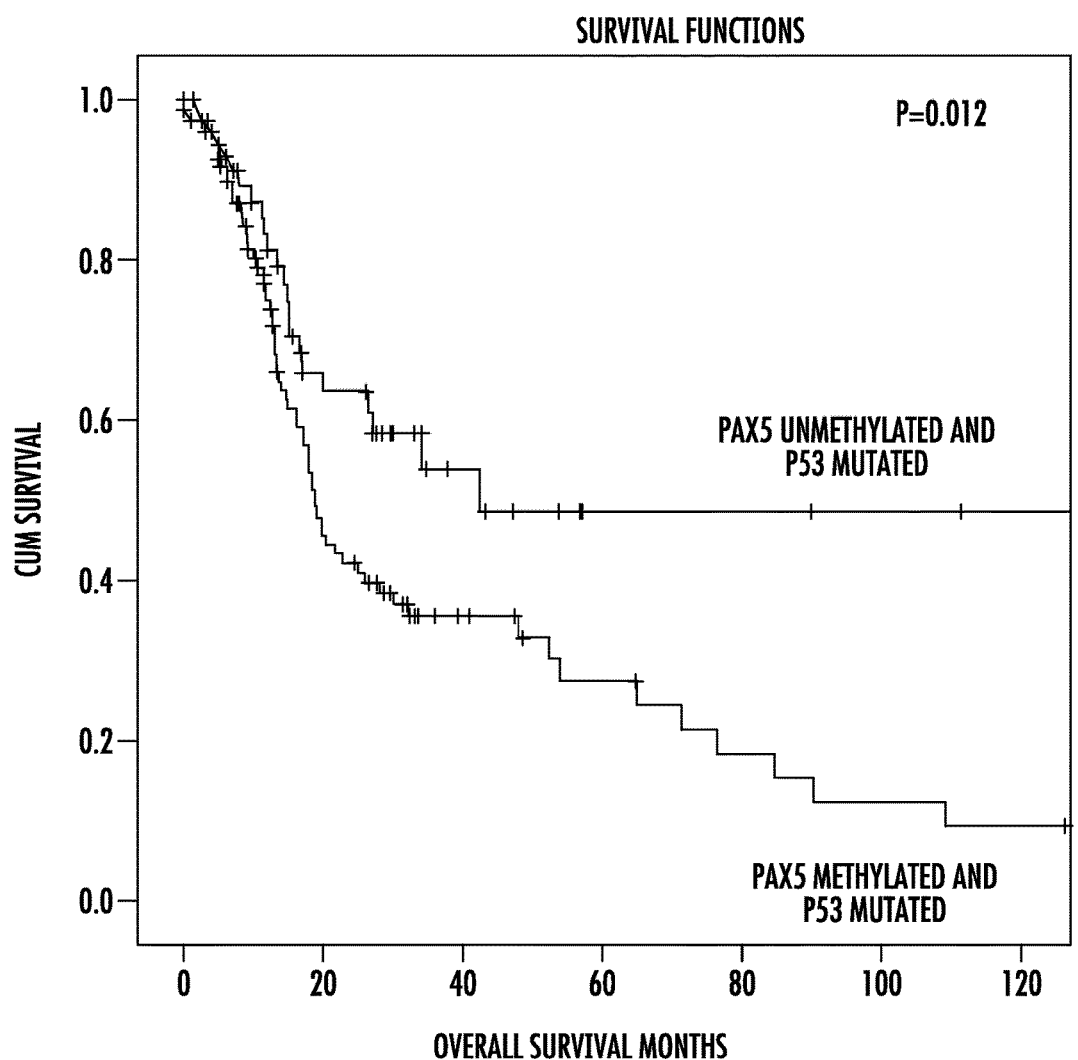
FIG. 9 is a Kaplan-Meier curve depicting the difference in survival of patients having PAX5 unmethylated and p53 mutation vs. PAX5 methylated and p53 mutation. This finding illustrates one of the inventive concepts regarding methylation of PAX genes and increased severity of cancer in subjects.

In accordance with some other embodiments, the present inventors found that PAX1 was the most frequently methylated and downregulated gene. In addition to that, several HOX family genes, some of which are known to interact with NOTCH signaling, were prominent in the present list of methylated genes in HNSCC (FIG. 9). The present invention suggests an interaction between NOTCH1 and PAX1 through the HOX family of transcription factors. PAX1 plays a role in sclerotome differentiation and has been shown to interact with homeobox genes which play a prominent role in normal development and in the control of cell proliferation (34).

Figure 4:
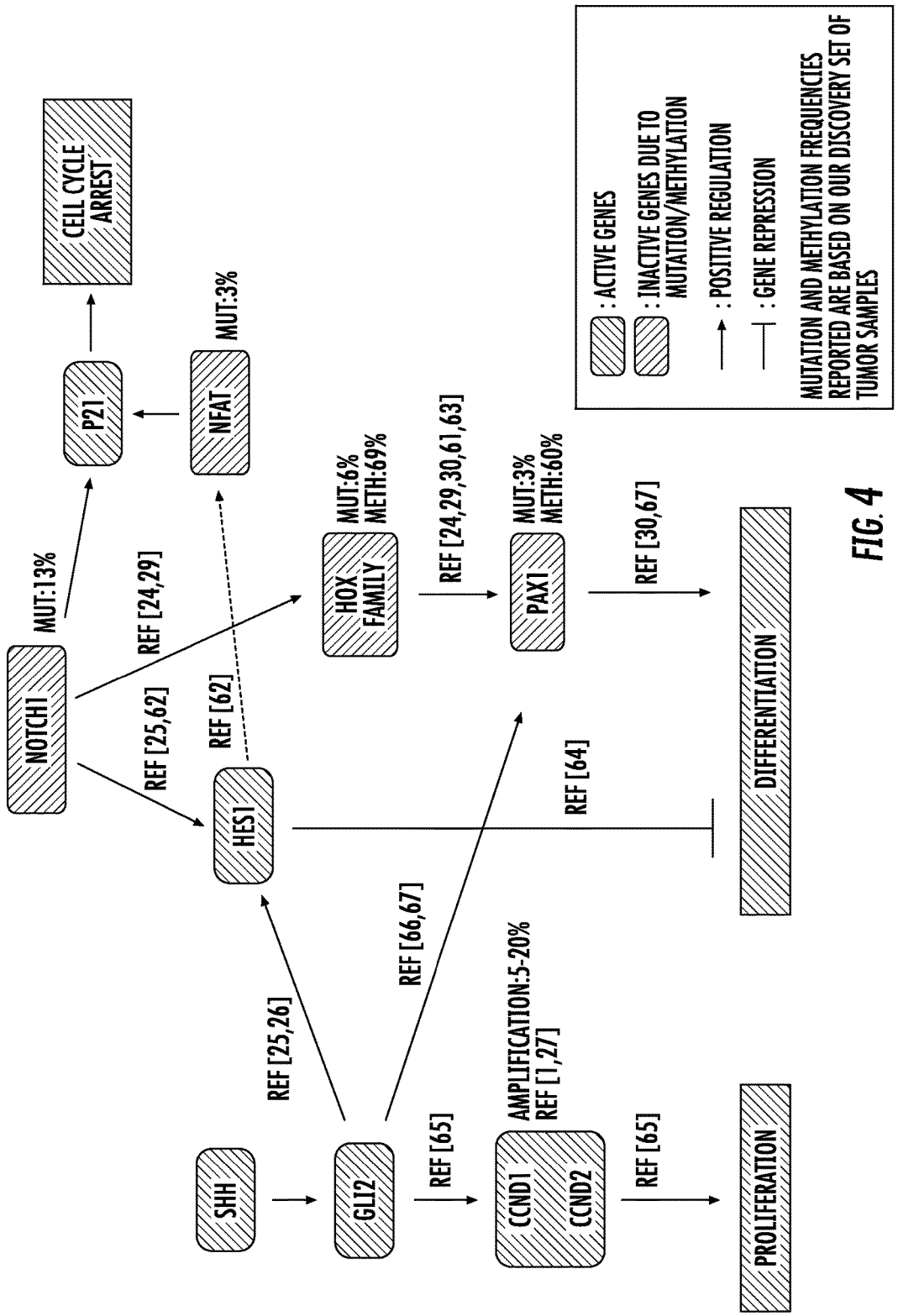
FIG. 4 depicts PAX1-NOTCH1 interplay through crosstalk of Hedgehog and Notch pathways in cell differentiation and proliferation signals. Notch1 induces p21 expression, either directly through the canonical pathway or indirectly through Hes1 and NFAT activation, leading in both cases to cell cycle arrest. Active Notch1 targets either the Hox family or Hes1. Hes1 is active and will block differentiation. The HOX family of transcription factors, downstream targets of Notch signaling, is frequently silenced, thus blocking the activation of PAX1 which is also downregulated in HNSCC and will not promote differentiation. PAX1 expression can also be induced by Shh through Gli2, which is active. Finally, proliferation is promoted through Gli2 interaction with CCND1 and CCND2.

Retinoid acid (RA) signaling acts via Hox gene pathways (35, 36), some of which are able to regulate PAX1 through canonical NOTCH1 expression. These interactions are described in FIG. 4.

The PAX genes, a family of nine transcription factors which act as cell lineage specific regulators of the tissues where they are normally expressed, are now also recognized as important factors in cancer progression. PAX genes, similarly to the NOTCH gene family, may play previously unrecognized fundamental roles in balancing proliferation and differentiation signals, two conceptually opposite cellular processes in canonical cancer research. The PAX family of genes may ultimately, following Waddington's epigenetic landscape metaphor, be part of an epigenomic mediated switch between cancer initiation and cancer maintenance pathways, which stochastically drive cancer progression, immune system avoidance, acquisition of tumor resistance, and establishment of metastatic disease. Loss of NOTCH1 function due to mutation, or mutation/methylation-dependent silencing of downstream genes, such as PAX1 or the HOX family genes, is likely to abrogate normal cell differentiation.

Clinically, p53 mutation has been shown time and again to be among the worst molecular alterations in patients with HNSCC. Patients that harbor p53 mutant tumors are more likely to relapse after complete resection and radiation therapy. Remarkably, PAX methylated tumors in the TCGA cohort also fair poorly, and even in tumors that already harbor a p53 mutation, the addition of PAX5 methylation significantly diminishes survival. Thus, in accordance with an embodiment, the present invention provides methods of identification of specific genes inactivated by both mutation and promoter methylation which can quickly identify new relevant prognostic subsets of HNSCC patients.

Because of the heterogeneity of tumors from individual to individual, even tumors of the same organ or type, any single marker may not yield sufficient sensitivity. Thus it may be beneficial to use panels of markers to increase the sensitivity of risk. One particular panel of markers that may be used for detection of increased risk of poor treatment outcome in head and neck squamous cell carcinoma and in particular oral squamous cell carcinoma comprises PAX1 and PAX5.

Tests can be carried out on any suitable sample that is likely to yield squamous cells or squamous cell nucleic acids. Particular samples which can be used include tissue specimens, biopsy specimens, surgical specimens, saliva, nasal mucosa, leukoplakia, erythroplakia, leukoerythroplakia and cytological specimens. It may be beneficial to extract nucleic acids from the cells prior to testing. Some techniques of testing may not require pre-extraction. Some testing may be done on proteins which may or may not be extracted from the cells prior to testing for particular detection techniques.

In accordance with another embodiment of the present invention, it will be understood that the term "biological sample" or "biological fluid" includes, but is not limited to, any quantity of a substance from a living or formerly living patient or mammal. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

Any tests can be used to detect either hypermethylation, hypoexpression, or both. Suitable tests which can be used without limitation include lab-on-chip technology, microfluidic technologies, biomonitor technology, proton recognition technologies (e.g., Ion Torrent), and other highly parallel and/or deep sequencing methods. Once a biomarker is known as epigenetically silenced, either hypermethylation or hypoexpression may be used as in indicator of silencing.

It will be understood by those of ordinary skill, that there are a number of ways to detect DNA methylation, and these are known in the art. Examples of preferred methods of detection of methylation of DNA in a sample include the use of QMSP, oligonucleotide methylation tiling arrays, paramagnetic beads linked to MBD2, i.e., BeadChip assays and HPLC/MS methods. Other methods include methylation-specific multiplex ligation-dependent probe amplification (MS-MPLA), bisulfate sequencing, and assays using antibodies to DNA methylation, i.e., ELISA assays. The methylation state information gathered from these methods can be generated using any type of microprocessor or computing device.

As used herein, the term "methylation state" means the detection of one or more methyl groups on a cytidine in a target site of the DNA in the sample.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In accordance with an embodiment, the present invention provides a method for identifying a subject having an increased risk for a poor survival outcome having head and neck squamous cell cancer comprising: a) obtaining nucleic acid from a test sample from the subject, wherein the test sample is from a specimen selected from the group consisting of a tissue specimen, a biopsy specimen, a surgical specimen, saliva, and a cytological specimen; b) performing bisulfite modification to the nucleic acid in a); c) performing quantitative methylation specific PCR (QMSP) on bisulfite modified nucleic acid from b) using the PCR primers and probes specific for the promoter region of one or more genes of interest, wherein the one or more genes of interest are selected from the group consisting of PAX1, PAX5, ZIC4, and PLCB1, and the primers and probes are selected from the group consisting of SEQ ID NOS: 4-15; d) determining the promoter methylation level of the promoter regions of the one or more genes of interest in the nucleic acid from the test sample of the subject; e) providing a reference non-neoplastic test sample, wherein the test sample is from a specimen selected from the group consisting of a tissue specimen, a biopsy specimen, a surgical specimen, saliva, and a cytological specimen; f) comparing the level of promoter methylation of the one or more genes of interest from the test sample of the subject, to the level of promoter methylation of the one or more genes of in a reference non-neoplastic test sample; g) identifying said subject as having an increased risk of poor survival outcome having head and neck squamous cell cancer when the level of promoter methylation of the one or more genes of interest in the test sample of the subject, is increased relative to the level of promoter methylation of the one or more genes of interest in a reference non-neoplastic test sample indicating epigenetic silencing of the one or more genes of interest; and h) adjusting or modifying the planned treatment of the subject as a result of the increased risk of poor survival in the subject having head and neck squamous cell cancer.

It will be understood by those of ordinary skill, that a diagnosis of an increased risk of poor treatment outcome in HNSCC can be made by detection of increased methylation of PAX1, and/or PAX5 and/or, ZIC4, and/or PLCB1.

In some embodiments, the assessment of the increased risk of poor treatment outcome of subjects having HNSCC can be determined with the additional assessment of whether the tumor has a p53 mutation. One of skill in the art would understand that in such cases, the increased risk of poor outcome is increased over subjects having tumors without p53 mutations.

Expression of a gene can be assessed using any means known in the art. Typically expression is assessed and compared in test samples and control samples which may be normal, non-malignant cells. The test samples may contain cancer cells or pre-cancer cells or nucleic acids from them. Samples will desirably contain squamous cells. Samples may contain mixtures of different types and stages of cancer cells. Either mRNA (or cDNA) or protein can be measured to detect expression which may be used as an indicator of epigenetic modification. Methods employing hybridization to nucleic acid probes can be employed for measuring specific mRNAs. Such methods include using nucleic acid probe arrays (microarray technology), in situ hybridization, and using Northern blots. Messenger RNA can also be assessed using amplification techniques, such as RT-PCR. Advances in genomic technologies now permit the simultaneous analysis of thousands of genes, although many are based on the same concept of specific probe-target hybridization. Sequencing-based methods are an alternative; these methods may be based on short tags, such as serial analysis of gene expression (SAGE) and massively parallel signature sequencing (MPSS). Differential display techniques provide yet another means of analyzing gene expression; this family of techniques is based on random amplification of cDNA fragments generated by restriction digestion, and bands that differ between two tissues identify cDNAs of interest.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a squamous cell cancer. As used herein the term "squamous cell cancer" refers to an invasive malignant tumor derived from squamous tissue that can metastasize to other areas of the body, e.g., a carcinoma. Preferably, the squamous cell cancer is HNSCC.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein. Preferably, the cancer is a metastatic cancer.

The phrase "controls or control materials" refers to any standard or reference tissue or material that has not been identified as having cancer. The degree of methylation is calculated by determining the amount of 2'-deoxycytidine (2dc) and 5-methyl-2'-deoxycytidine (5mdc) in the unknown DNA sample and comparing the amount of 5mdc relative to the amount of 5mdc+2dc in the sample and generating a ratio. This is then compared to the degree of methylation of a control sample.

The nucleic acids used as primers in embodiments of the present invention can be constructed based on chemical synthesis and/or enzymatic ligation reactions using procedures known in the art. See, for example, Sambrook et al. (eds.), *Molecular Cloning, A Laboratory Manual*, 3$^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleotide sequences used herein are those which hybridize under stringent conditions preferably hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C.

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

In accordance with another embodiment, the present invention provides a kit for assessing a subject having an increased risk for a poor survival outcome having head and neck squamous cell cancer in a test sample containing head and neck squamous cells or nucleic acids from head and neck squamous cells, said kit comprising in a package: a reagent that (a) modifies methylated cytosine residues but not non-methylated cytosine residues, or that (b) modifies non-methylated cytosine residues but not methylated cytosine residues; and at least one set of oligonucleotide primers that specifically hybridizes under amplification conditions to a region of at least one gene selected from the group consisting of PAX1, PAX5, ZIC4, and PLCB1; and the primers and probes are selected from the group consisting of SEQ ID NOS: 4-15, wherein the region is within about 1 kb of said gene's transcription start site; and instructions for assessing head and neck squamous cell cancer using the reagents.

It will be understood by those of ordinary skill in the art that the inventive methods and kits described herein can be used in conjunction with other diagnostic and therapeutic methods.

The methods of the present invention can be used to monitor efficacy of a therapeutic regimen, for example, whether a chemotherapeutic agent or a biological agent, such as a polynucleotide. Testing can also be used to determine what therapeutic or preventive regimen to employ on a patient. Moreover, testing can be used to stratify patients into groups for testing agents and determining their efficacy on various groups of patients. Such uses characterize the cancer into categories based on the genes which are epigenetically silenced and/or the amount of silencing of the genes. In the case of a diagnosis or characterization, information comprising data or conclusions can be written or communicated electronically or orally. The identification may be assisted by a machine. Communication of the data or conclusions may be from a clinical laboratory to a clinical office, from a clinician to a patient, or from a specialist to generalist, as examples. The form of communication of data or conclusions typically may involve a tangible medium, or physical human acts. In a preferred embodiment, the methods allow a clinician or clinical laboratory to determine that a subject has an increased risk of poor treatment outcome from HNSCC and can change the therapeutic regimen to one that is more aggressive, for example.

Kits according to the present invention are assemblies of reagents for testing methylation and/or silencing. They are typically in a package which contains all elements, optionally including instructions. Instructions may be in any form, including paper or digital. The instructions may be on the inside or the outside of the package. The instructions may be in the form of an internet address which provides the detailed manipulative or analytic techniques. The package may be divided so that components are not mixed until desired.

Components of the kits of the present invention may be in different physical states. For example, some components may be lyophilized and some in aqueous solution. Some may be frozen. Individual components may be separately packaged within the kit. The kit may contain reagents, as described above for differentially modifying methylated and non-methylated cytosine residues. Desirably the kit will contain oligonucleotide primers which specifically hybridize to regions within 1 kb of the transcription start sites of the selected genes/biomarkers. Additional markers may be used. Typically the kit will contain both a forward and a reverse primer for a single gene or marker. If there is a sufficient region of complementarity, e.g., 12, 15, 18, or 20 nucleotides, then the primer may also contain additional nucleotide residues that do not interfere with hybridization but may be useful for other manipulations. Exemplary of such other residues may be sites for restriction endonuclease cleavage, for ligand binding or for factor binding or linkers or repeats. The oligonucleotide primers may or may not be such that they are specific for modified methylated residues. The kit may optionally contain oligonucleotide probes. The probes may be specific for sequences containing modified methylated residues or for sequences containing non-methylated residues. The kit may optionally contain reagents for modifying methylated cytosine residues. The kit may also contain components for performing amplification, such as a DNA polymerase (particularly a thermostable DNA polymerase) and deoxyribonucleotides, labeled or not. Means of detection may also be provided in the kit, including detectable labels on primers or probes. Kits may also contain reagents for detecting gene expression. Such reagents may include probes, primers, or antibodies, for example. In the case of enzymes or ligands, substrates or binding partners may be used to assess the presence of the marker. Kits may contain 1, 2, 3, 4, or more of the primers or primer pairs of the invention. Kits that contain probes may have them as separate molecules or covalently linked to a primer for amplifying the region to which the probes hybridize. Other useful tools for performing the methods of the invention or associated testing, therapy, or calibration may also be included in the kits, including buffers, enzymes, gels, plates, detectable labels, vessels, etc. Kits may-include tools for collecting suitable samples, such as tools for collecting oral swabs, oral biopsies, and endoscopes.

The term "biologically active" as used herein means an enzyme or protein having structural, regulatory, or biochemical functions of a naturally occurring molecule.

The term "reacting" in the context of the embodiments of the present invention means placing compounds or reactants in proximity to each other, such as in solution, in order for a chemical reaction to occur between the reactants.

As used herein, the term "treat," as well as words stemming therefrom, includes diagnostic and preventative as well as disorder remitative treatment.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

As used herein, the term "increased risk of poor outcome or poor treatment outcome" means that subjects identified as having one or more of the genes identified as being hypermethylated when compared to controls, are more likely to relapse after complete resection and radiation therapy and/or chemotherapy, and have a significant diminished chance of survival.

EXAMPLES

Patient selection. Head and Neck Squamous Cell Carcinoma (n=91) and uvulopalatopharyngealplasty (UPPP) patients (n=35) were consented for this study at Johns Hopkins Medical Institutions hospitals and MD Anderson Cancer Center. All participants signed a consent form that clearly explained the risks and benefits of the study. The study was approved by the Ethics Committee of each participating hospital, as well as by the Johns Hopkins Institutional Review Board.

JHU Tissue preparation. Fresh-frozen surgically resected tissue and matched blood were obtained from patients at Johns Hopkins Medical Institutions in Baltimore. Tissue samples were frozen in liquid nitrogen and stored in −80° C. at the Head and Neck Cancer Research Laboratory of the Department of Otolaryngology at Johns Hopkins School of Medicine. Tissue was analyzed by frozen section histology to estimate neoplastic cellularity. In order to enrich the samples for neoplastic cells, normal tissue was removed from the samples using macro-dissection based on the frozen section histology. HPV tumor status was determined for oropharyngeal tumors per standard clinical care using in-situ hybridization. Hybridization was performed using the HPV III Family16 probe set that captures HPV genotypes 16, 18, 33, 35, 45, 51, 52, 56 and 66. Punctate hybridization signals localized to the tumor cell nuclei defined an HPV associated tumor. HPV16-positive controls included an HPV16-positive oropharyngeal cancer and the SiHa and CaSki cell lines. HPV tumor status was also determined by E6/E7 PCR primer amplification in all the HNSCC samples that were processed for Methylation Binding Domain sequencing.

MD Anderson Tissue preparation. Fresh-frozen surgically resected tumor and matched non-malignant adjacent tissue were obtained from consented patients treated for HNSCC at the University of Texas M.D. Anderson Cancer Center, under an Institutional Review Board approved protocol. Frozen tissue was embedded in optimal cutting temperature compound and cryosections from the top and middle of specimens were stained with hematoxylin and eosin prior to being evaluated by a pathologist for the presence of >60% tumor nuclei content or absence of tumor (i.e., normal). Samples that passed this criterion were sectioned all the way through and washed once in PBS prior to isolating genomic DNA using an ArchivePure DNA purification kit (Gaithersburg, Md.).

Methylated Binding Domain Sequencing (MBD-seq). Tissue samples were digested with 1% SDS and 50 µg/mL proteinase K (Boehringer Mannheim) at 48° C. overnight, followed by phenol/chloroform extraction and ethanol precipitation of DNA. 2 µg of DNA was sonicated to a modal size of ~150-250 bp, and end-repaired using the NEBNext SOLiD DNA library preparation kit end-repair module following the manufacturer's protocol (New England Biolabs). After column-purification (using the Qiagen PCR purification kit), SOLiD P1 and P2 adapters lacking 5' phosphate groups (Life Technologies) were ligated using the NEBNext adapter ligation module and column-purified, and subjected to nick-translation by treating with Platinum Taq polymerase to remove the nick.

The resulting library was divided into two fractions, a total input fraction, and an enriched methylated fraction. The enriched methylated fraction was then subjected to affinity enrichment of methylated DNA fragments by using 6× His-MBD2-MBD polypeptides immobilized on magnetic beads as described previously (38-40). The resulting enriched methylated fraction and the total input fraction were then subjected to library amplification using the NEBNext amplification module according to the manufacturer's protocols, using 4-6 cycles for the total input, and 10-12 cycles for the enriched methylated fractions. Library fragments that were between 200-300 bp were size selected after agarose gel electrophoresis.

Massively parallel sequencing of MBD-seq libraries. The libraries were then subjected to emulsion PCR and bead enrichment following the SOLiD emulsion PCR protocol (Life Technologies). The resulting beads were then deposited on the SOLiD flow cell and subjected to massively parallel 50 bp single-read sequencing on a SOLiD v4.0 sequencer octet segment, with one octet segment for the total input and another one for the enriched methylated fraction. Reads were aligned to hg19 using default settings in bioscope v1.3, with the exception of the bam output method, which was changed to alignment score.

MACS analysis and identification of differential methylation. For the purposes of the analysis we divided the genome into two broad regions: the greater promoter, was defined as the region encompassing 6000 bases upstream and 1,500 bases downstream from the transcription start site (TSS). From the functional genome distribution standpoint the greater promoter region, includes CpG sites in the proximal promoters, 1500 bases upstream from the described TSS, and 1500 bases downstream from the TSS, in the 5' untranslated region and exon 1. From the CpG content and neighborhood context the differentially methylated CpGs in HNSCC were located in CpG islands, CpG shores (regions 2000 bp upstream and downstream of but not inside CpG islands), CpG shelves (regions 2000 bp upstream and downstream of but not inside the shores), or as isolated CpGs in the area of the genome now defined as Open Sea.

Methylated regions were identified as peaks of aligned sequencing tags using MACS v1.4 software (12, 41, 42), which allows identification of peaks after accounting for both global and local biases using the total input fraction. To identify differentially methylated regions we first used stringent parameters to define presence and absence of methylation in each sample as follows: we used a low p-value cut-off ($p<10^{-6}$) to identify regions that are methylated, and another cut-off ($p>10^{-2}$) to identify those regions that have very little evidence for methylation. Next, for any given comparison of group A vs. group B (e.g. Group A=all tumors and Group B=all normals), we identified all regions that showed absence of methylation in all samples of Group A and presence of methylation in at least one sample from group B. All regions across samples with peak calls in Group B were then merged, and the number of such samples and the lowest p-value of the peaks for these samples were recorded as the aggregate differentially methylated region. The converse comparisons were performed to identify differentially methylated regions.

Methylation bumphunting for identification of differentially methylated regions. Differential methylation was also identified using an independent approach called bumphunting (13) that has been previously used to identify differential peaks in methylation data. Methylation bumphunting is a data analysis pipeline that effectively models measurement error, removes batch effects, detects regions of interest and attaches statistical uncertainty to regions identified as differentially methylated (13). Reported functionally relevant findings have been generally associated with genomic regions rather than single CpGs, either CpG islands (43), CpG island shores (19), genomic blocks (44), or generic 2-kb regions (14). Epigenomic bumps may have greater variability in size and shape than MBD-seq peaks. For example, while MBD-seq peaks are usually roughly triangle shapes spanning several hundred base pairs, regions of differential DNA methylation may range from several hundred base pairs to several megabases (44). The methylation bumphunting algorithm also incorporates functionality to address specific situations that arise in cancer studies, in which a large number of bumps (thousands) are identified as differentially methylated and thus require the implementation of different approaches to correct for multiple testing comparisons. Cancer studies also use samples that are acquired, and often measured, across long periods of time.

While we were careful to avoid batch-effects during the DNA quantification, library preparation and MBD enrichment steps, we were unable to eliminate MBD-seq batch effects that arise on the SOLiD, since only four samples (including both enriched and input fractions) could be sequenced at a time, and each run spans approximately two weeks. Thus we had potentially 10 batches of samples. The batch removing functionality of bumphunting (45) potentially minimized the impact that these potential sources of batch effects may have had on our data (13).

Integration of MACS and bumphunting results. To identify the promoter regions that are differentially methylated in HNSCC when compared to normal oral mucosa, we intersected the list of methylated probes that discriminated between tumor and normal tissue identified with MACS with the list of methylated regions that discriminated between tumor and normal tissue identified with bumphunting. We used R (v3.00) to analyze the correlation of methylated promoter regions and HNSCC etiological factors.

Verification of MBD-seq results with HumanMethylation450K DNA BeadChip assay. Bisulfite modification of genomic DNA (2 µg) was performed with EpiTect Bisulfite Kit (QIAGEN) according to the manufacturer's protocol. We hybridized bisulfate converted DNA from normal (UPPP) tissue (n=16) and Head and Neck Squamous Cell Carcinoma (HNSCC) tissue (n=31) samples to HumanMethylation450K DNA BeadChip slides, which quantitatively interrogates over 99% of RefSeq genes with multiple probes per gene, 96% of CpG islands from the UCSC database gene promoters, and over 400 microRNA gene promoters at single-nucleotide resolution. The 20 samples that were sequenced with MBD-seq were contained in the 47 samples that were hybridized to the Illumina 450K slides.

The Infinium DNA Methylation 450K BeadChip assay detects cytosine methylation at individual CpGs based on highly multiplexed and complex genotyping. Briefly, each sample is measured on a single array, in two different color channels (red and green). Each array measures roughly 450,000 CpG positions. Each CpG is associated with two measurements: a methylated measurement and an un-methylated measurement. These two values can be measured in one of two ways: using a "Type I" design or a "Type II" design. CpGs measured using a Type I design are measured using a single color, with two different probes in the same color channel providing the methylated and the unmethylated measurements. CpGs measured using a Type II design are measured using a single probe, and two different colors provide the methylated and the unmethylated measurements (46).

Practically, this implies that on this array there is not a one-to-one correspondence between probes and CpG positions. The previous generation 27K methylation array uses only the Type I design. A beta (β) value was generated by both Type I and Type II design probes to denote the methylation level of the CpG loci using the ratio of intensities between methylated and unmethylated alleles (β value=Methylation intensity/Methylation+unmethylated intensity of the given CpG locus). Two idat files were generated for each sample with the raw data from the Type I and Type II probes.

Bioinformatics for 450K data. Bioinformatics strategies were used for background correction, normalization and data analysis of differentially methylated genomic regions between tumor, and normal tissue. As with the analysis of methylation sequencing data, we used two different analytic pipelines: a pipeline designed to capture the variability in methylated signals across the arrays using an F-test as previously described (5) and the bumphunting pipeline (13). In order to identify significant differentially methylated peaks between UPPP and HNSCC samples we: a) identified and eliminated extreme outliers that clearly skewed and interfered with our ability to discriminate real methylation differences; b) performed subset analyses to identify differentially methylated CpG Islands, CpG shores, CpG shelf, enhancer regions and DMRs; c) identified differentially methylated regions between UPPP and tumor samples.

F-test analytic pipeline. The selection of significantly methylated CpGs in the Illumina 450K Infinium assay data was performed in a stepwise manner. An F-test was performed across all 47 samples to identify CpGs with a significant difference in β values between normal, and malignant tissue. Since the empirical p-values were calculated genome-wide, adjustment for multiple testing was performed. Rather than using a Bonferroni correction, which is very stringent, the p-values were transformed into q-values, which are measures of significance in terms of the false discovery rate (FDR) instead of the false positive rate normally associated with p-values. Q-values were computed from the empirical pvalues using the Benjamin and Hochberg correction. Probes with q-values less than 0.05 were deemed statistically significant and were included in the CpG list. We then selected only those CpGs that showed a methylation difference of at least 0.25 between cancer and normal tissues and a beta value of at least 0.3 in cancer, as previously described (5). All bioinformatics analyses were performed using R version 2.3.0.

450K-bumphunting analytic pipeline. We used an unreleased beta version of the minfi and bumphunter packages found in Bioconductor. The minfi package provides tools for analyzing Illumina's Methylation arrays, with a special focus on the new 450 k array for humans. At the moment Illumina's 27 k methylation arrays are not supported. The tasks addressed in this package include preprocessing, QC assessments, normalization, identification of interesting methylation loci and plotting functionality. The input data to this package are IDAT files, representing two different color channels prior to normalization (47).

The bump hunter methodology is meant to work on data with several biological replicates, similar to the lmFit function in limma. While the package is written using genomic data as an illustrative example, most of it is generalizable to other data types (with some one-dimensional location information). Bumphunter assumes data Yij where i represents (biological) replicate and lj represents genomic location. The use of j and lj is a convenience notation, allowing to discuss the "next" observation j+1 which may be some distance lj+1−lj away. Note that it is assumed in this notation that all replicates have been observed at the same set of genomic locations.

The basic statistical model is the following:

$$Y_{ij} = \beta_0(l_j) + \beta_1(l_j) X_j + \varepsilon_{ij}$$

with i representing subject, lj representing the jth location, Xj is the covariate of interest (for example Xj=1 for cancer cases and Xj=0 for controls), εij is measurement error, β0(1) is a baseline function, and β1(1) is the parameter of interest, which is a function of location. The model assumes that β1(1) will be equal to zero over most of the genome, and it wants to identify stretches where β1(1)≠0, called bumps (48).

Integration of F-test and 450K-bumphunting results. To identify the promoter regions that are differentially methylated in HNSCC when compared to normal oral mucosa, we intersected the list of methylated probes that discriminated between tumor and normal tissue identified with the F-test with the list of methylated regions that discriminated between tumor and normal tissue identified with 450K-bumphunting.

mRNA expression arrays. Total RNA was isolated from normal (UPPP) tissue (n=16) and Head and Neck Squamous Cell Carcinoma (HNSCC) tissue (n=16) samples by using Tri-reagent. cDNA was made, and hybridized to Affymetrix GeneST1.0 Arrays (Affymetrix) according to manufacturer's instructions. Six of these samples were also sequenced with MDB-seq. The data obtained from CEL files was background corrected with RMA, quantile normalized before an ANOVA was used to determine the Fold Change difference in log-transformed intensities between Tumor and Normal samples.

Analysis of functional annotation. Enrichment analysis of functional themes (Analysis of Functional Annotation, AFA) was performed to capture biological processes over-represented in the various conditions under investigation. This unbiased computational approach, conceptually similar to Gene Set Enrichment Analysis (GSEA) (49), enables the interpretation of genome-wide data through the identification and visualization of information encompassing distinct biological concepts, and was previously successfully used to integrate and interpret both differential gene expression and methylation data (50). A chi-squared test was applied to test whether each Functional Gene Set (FGS) was over-represented in any of the gene list associated with any of the investigated contrasts/conditions (e.g. gene associated with methylated promoters in HNSCC). In the present inventive methods, individual, nonredundant genes, as annotated in the NCBI Entrez gene database (R/Bioconductor package org.Hs.eg.db version 2.4.6) were used as the total gene space, and contingency tables were used to identify gene sets over-represented in the investigated conditions.

Correction for multiple hypothesis testing was obtained separately for each FGS collection, by applying the Benjamini and Hochberg method (51) as implemented in the multtest R/Bioconductor package. Overall, this approach is analogous to Gene Set Enrichment Analysis (GSEA) (49, 52-55), and has already been successfully applied in other studies (50, 56-58). The heatmaps' color bar represents the negative $\log_{10}$ False Discovery Rate (FDR). For each gene set collection the sets for which at least one condition showed FDR<0.01 were reported. The top 150 conditions were reported when too many gene sets where retrieved (data not shown).

Validation of promoter methylation in Prevalence Cohort and TCGA dataset. qMSP was used to validate in a Prevalence Cohort of 76 tumors in which we had previously identified somatic mutations in TP53, NOTCH1, CDKN2A, PIK3CA, FBXW7, and HRAS and in 19 UPPP normal control tissue samples. We examined promoter methylation in three of the genes that were included in our final list of mutated and methylated genes and that were methylated in at least 40% of the Discovery Cohort samples: PAX1, PAX5, PLCB1 and ZIC4. Bisulfite-modified DNA was used as a template for fluorescence-based real-time PCR, as previously described (59). Amplification reactions were carried out in duplicate in a final volume of 20 μL that contained 3 μL of bisulfate-modified DNA; 600 nM concentrations of forward and reverse primers; 200 nM probe concentration; 0.6 U of platinum Taq polymerase (Invitrogen, Frederick, Md.); 200 μM concentrations each of dATP, dCTP, dGTP and dTTP; and 6.7 mM $MgCl_2$. Primers and probes were designed to specifically amplify the promoters of the genes of interest and the promoter of a reference gene, ACTB; primer and probe sequences are provided in table 1. Amplifications were carried out in 384-well plates in a 7900HT sequence detector (Applied Biosystems, Foster City, Calif.) using the following conditions: 95° C. for 3 minutes, followed by 50 cycles at 95° C. for 15 seconds and 60° C. for 1 minute. Results were analyzed by a sequence detector system (SDS 2.4; Applied Biosystems). Each plate included patient DNA samples, positive and negative controls. Serial dilutions (60-0.006 ng) of the in vitro methylated DNA were used to construct a calibration curve for each plate. All samples were within the assay's range of sensitivity and reproducibility based on amplification of an internal reference standard (threshold cycle [CT] value for ACTB of 40). The relative level of methylated DNA for each gene in each sample was determined as a ratio of methylation specific PCR-amplified gene to ACTB (reference gene) and then multiplied by 1000 for easier tabulation (average value of duplicates of gene of interest divided by the average value of duplicates of ACTB×1000). The samples were categorized as unmethylated or methylated based on detection of methylation above a threshold set for each gene. This threshold was determined by using receiver operating characteristic (ROC) curves in STATA (v.11) to analyze the levels and distribution of methylation in UPPPs. We used the Mann Whitney U test in SPSS (v.13) to analyze the qMSP results.

Pathway Integration. We performed a review study to identify cancer pathways potentially impacted by the strong interplay we observed between somatic mutations in p53 and NOTCH1 and gene downregulation associated to PAX1 and PAX5 promoter methylation in HNSCC. Our literature search revealed that p53-PAX5 interactions are implicated in apoptotic and/or proliferating signals. The mechanism through which PAX5 acts in B-cell differentiation is well established. Recent studies identified some of these interactions as well in solid tumors, but little has been shown so far. The inventive methods also led us to show an interaction

TABLE 1

Primers and probes for quantitative methylation specific PCR

| Gene | Forward 5'-3' | Probe FAM-3' TAMRA | Reverse 5'-3' | Amplicon length |
|---|---|---|---|---|
| HHIP | GTC GAT TTG GGT TTG GTT TGT (SEQ ID NO: 1) | ATT TCG CGT ATA CGC GTT TGT GTT (SEQ ID NO: 2) | AAA CTC ATC CTC GCC GAA A (SEQ ID NO: 3) | 102 bp |
| PAX1 | TCG TTA GGG AGA AAG GAA TTT GT (SEQ ID NO: 4) | TTT CGT CGG TCG CGT TTG GG (SEQ ID NO: 5) | TAA ATC CGA CGC CCT CCT A (SEQ ID NO: 6) | 99 bp |
| PLCB1 | GAT GTG TTG AAT GGT GCG TTT (SEQ ID NO: 7) | CGG AGG AGT AGA ATT CGT CGC GAT T (SEQ ID NO: 8) | CGA ACC GAT CAA CCG AAA CTA (SEQ ID NO: 9) | 83 bp |
| ZIC4 | GGT TTA GGA GGA AGG GTA TTC (SEQ ID NO: 10) | TTT AGT CGG TCG TCG TAT TGG TTT (SEQ ID NO: 11) | AAA CTA CGA ACC CTA CGA AA (SEQ ID NO: 12) | 127 bp |
| PAX5 | GCG TAA GAG AGA CGA AGG TAA G (SEQ ID NO: 13) | AGA GGT TCG CGT AGT TTC GTC GG (SEQ ID NO: 14) | ATA TTC GCG AAC ACC TCT ACT AC (SEQ ID NO: 15) | 112 bp |
| β-actin | TGG TGA TGG AGG AGG TTT AGT AAG T (SEQ ID NO: 16) | ACC ACC ACC CAA CAC ACA ATA ACA AAC ACA (SEQ ID NO: 17) | AAC CAA TAA AAC CTA CTC CTC CCT TAA (SEQ ID NO: 18) | |

TCGA data analysis. Publicly available HNSCC Illumina 450K methylation and exome sequencing data was downloaded from the TCGA web site (cancergenome.nih.gov) and the cBioPortal for Cancer Genomics (bioportal.org/public-portal/) using R (v3.0.0). Publicly available exome mutation data for TP53 and NOTCH1 and beta values for all PAX1 and PAX5 450K array probes were extracted for all HNSCC samples analyzed by the TCGA project that had paired methylation and mutation data for the genes of interest (n=279). Only the 450K probes located in TSS1500, TSS200 and 1st exon, as per the manufacturer's annotation, were used to create the contingency tables for methylation and mutation analyses.

Contingency tables of mutational and methylation events. Contingency tables were used to examine the association between exonic mutations of TP53, CDKN2A, HRAS, FBXW7, and NOTCH1 and promoter methylation of ZIC4, PAX1, PAX5, and PLCB1. The MacNemar test for paired data was implemented in R (version 3.0.0) to evaluate the association between mutations and promoter methylation. Cox regression analysis was used to assess overall survival and survival curves were generated using the Kaplan-Meier method.

between NOTCH1 and PAX1 through the HOX family genes; and also with the Hedgehog pathway through Hes1, in which the well-established CCND1 amplification plays an important role (60-73).

Example 1

Figure 5:
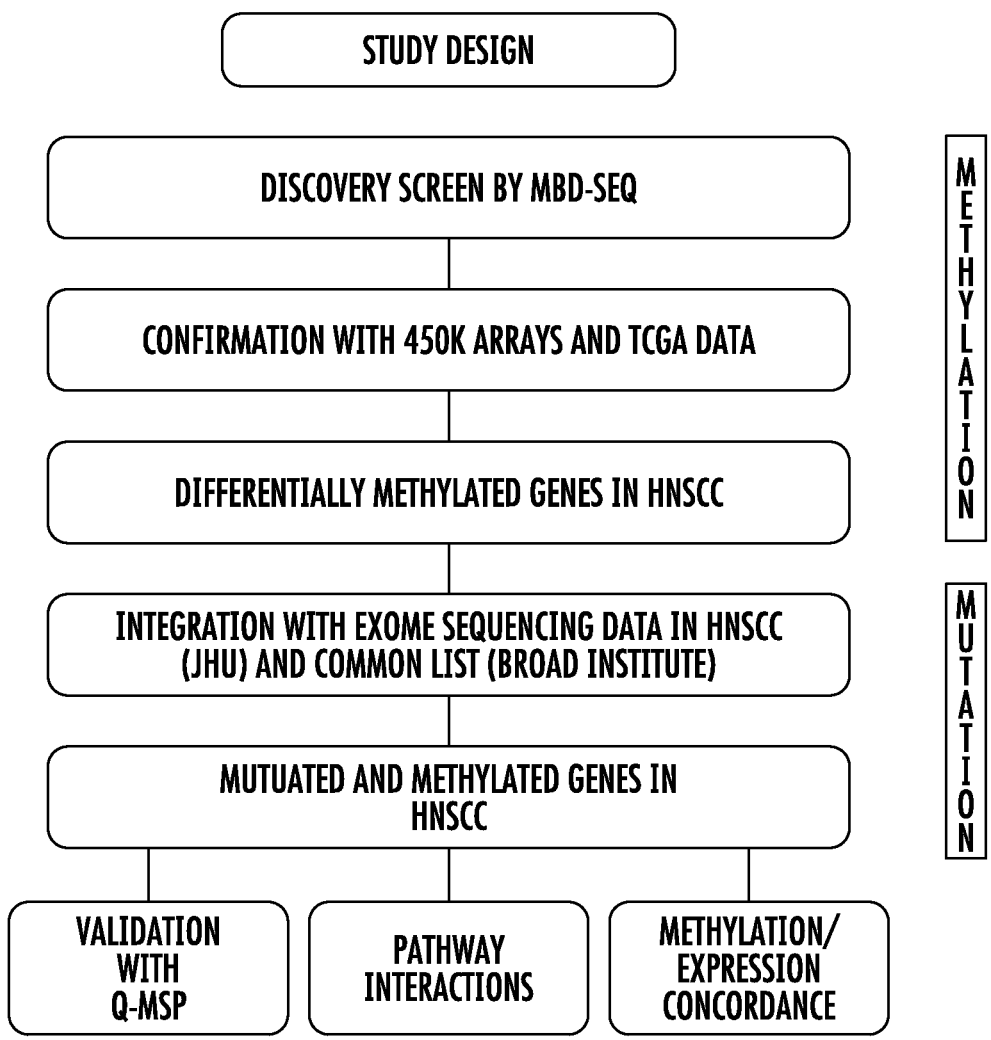
FIG. 5 depicts the workflow of the methods of the present invention. A schematic representation of the integrative approach we used to unmask concomitant genetic and epigenetic deregulation in HNSCC is provided.

We characterized the HNSCC methylome using a methylated DNA binding domain based sequencing (MBD-seq) approach similar in principle to what has been described previously (11), but with significant modifications (see examples above and FIG. 5). This analysis was carried out on a subset of tumors from the same Discovery Cohort in which Agrawal et al discovered and mapped mutations in HNSCC (1), comprising ten patients and ten frequency matched normal controls (uvulopalatopharyngoplasty tissue samples—UPPP). The ten tumor samples were obtained before chemotherapy or radiation treatment, ensuring that the changes we identified are truly reflective of tumor biology, and were micro-dissected to achieve a neoplastic cellularity of greater than 60%. Following MBD-seq, an average of 48.9 million 50 bp reads was obtained for each sample, with an average of 68% of these reads aligning to the hg19 genome, 67% of which were aligning uniquely (data not shown).

Figure 1A:
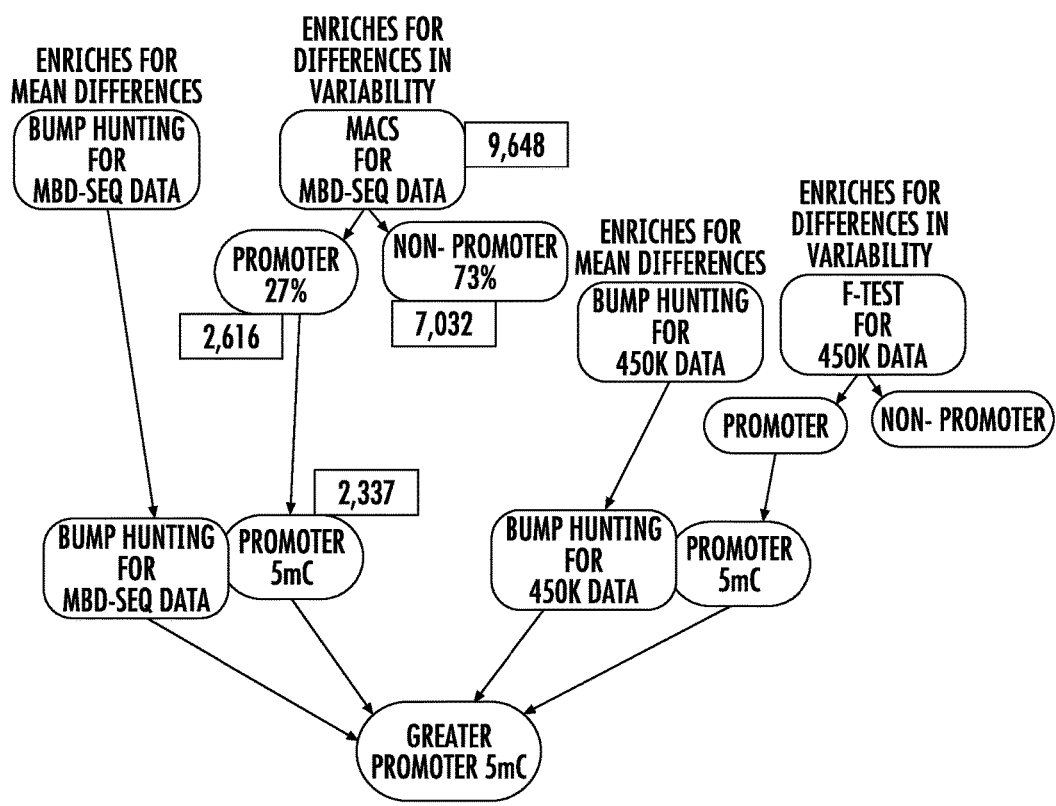
FIG. 1a is a schematic description of the analytic pipeline that was developed to unveil the HNSCC methylome. This pipeline enriches for genome-wide mean differences in CpG methylation and genome-wide differences in CpG methylation variability at each chromosomal location, for both, methylation sequencing data and methylation 450 k array data.
Figure 1B:
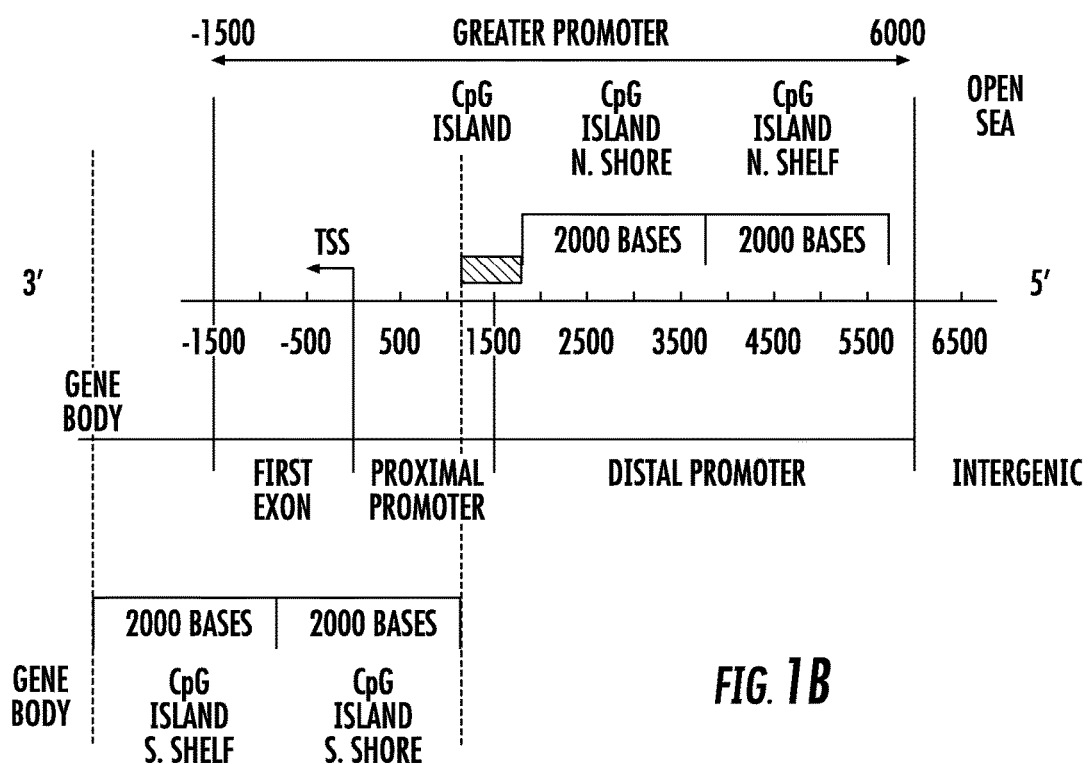
FIG. 1b is an illustration describing the greater promoter region we have focused our HNSCC methylome analysis on. Using a functional genomic distribution viewpoint we define five CpG genomic locations in relation to their distance to the Transcription Start Site: proximal promoter, distal promoter, first exon, gene body and intergenic locations. From a CpG content and neighborhood context viewpoint we define four CpG genomic locations in relation to their distance to the nearest CpG Island: CpG Island, CpG Island Shore, CpG Island Shelf, Open Sea and Gene Body. The Greater promoter window is fixed in relation to the TSS. Therefore, the location of CpG Islands will influence the number of significant sequencing reads and 450K probes per gene that is included in our analysis.

We used two independent and highly validated analytical pipelines, Model-based analysis of ChIP-seq (MACS) (12) and Bump hunting (13), to identify methylation changes across the HNSCC genome. MACS identified 9,648 alterations, 60% of which were gain in methylation events (FIG. 1a). The vast majority of the methylome changes identified by MACS (73%) were observed outside of the greater promoter region, which we defined as the region 1,500 bases downstream and 6,000 bases upstream from the TSS (FIG. 1b). Within the greater promoter region, most (89%) were gain of methylation events (data not shown). The majority of the methylation loss identified by MACS (93%) occurred outside the promoter region. These genome-wide methylation motifs were integrated with the DMRs identified by Bumphunting to obtain the first detailed next-gen analysis of the HNSCC methylome (tables 2 and 3 below).

TABLE 2

Distribution of methylated regions identified by two separate algorithms used to analyze MBD-seq Data: MACS and Bumphunting

|  | MACS | | Bumphunting | |
| --- | --- | --- | --- | --- |
| methylated | 5760 | 60% | 11063 | 86% |
| unmethylated | 3888 | 40% | 1764 | 14% |
| promoter | 2616 | 27% | 6038 | 47% |
| non-promoter | 7032 | 73% | 6804 | 53% |
| methylated promoter | 2337 | 41% | 5896 | 53% |
| methylated non-promoter | 3242 | 59% | 5166 | 47% |
| unmethylated promoter | 279 | 7% | 126 | 7% |
| un methylated non-promoter | 3609 | 93% | 1638 | 93% |

TABLE 3

Distribution of methylated regions identified by two separate algorithms used to analyze 450K Data: F-Test and Bumphunting

|  | F-test | | Bumphunting | |
| --- | --- | --- | --- | --- |
| methylated | 9119 | 50% | 4365 | 60% |
| unmethylated | 8999 | 50% | 2906 | 40% |
| promoter | 9249 | 51% | 1553 | 21% |
| non-promoter | 8869 | 49% | 5718 | 79% |
| methylated promoter | 4334 | 48% | 948 | 22% |
| methylated non-promoter | 4785 | 52% | 3417 | 78% |
| unmethylated promoter | 4915 | 55% | 605 | 21% |
| un methylated non-promoter | 4084 | 45% | 2301 | 79% |

Example 2

Figure 1C:
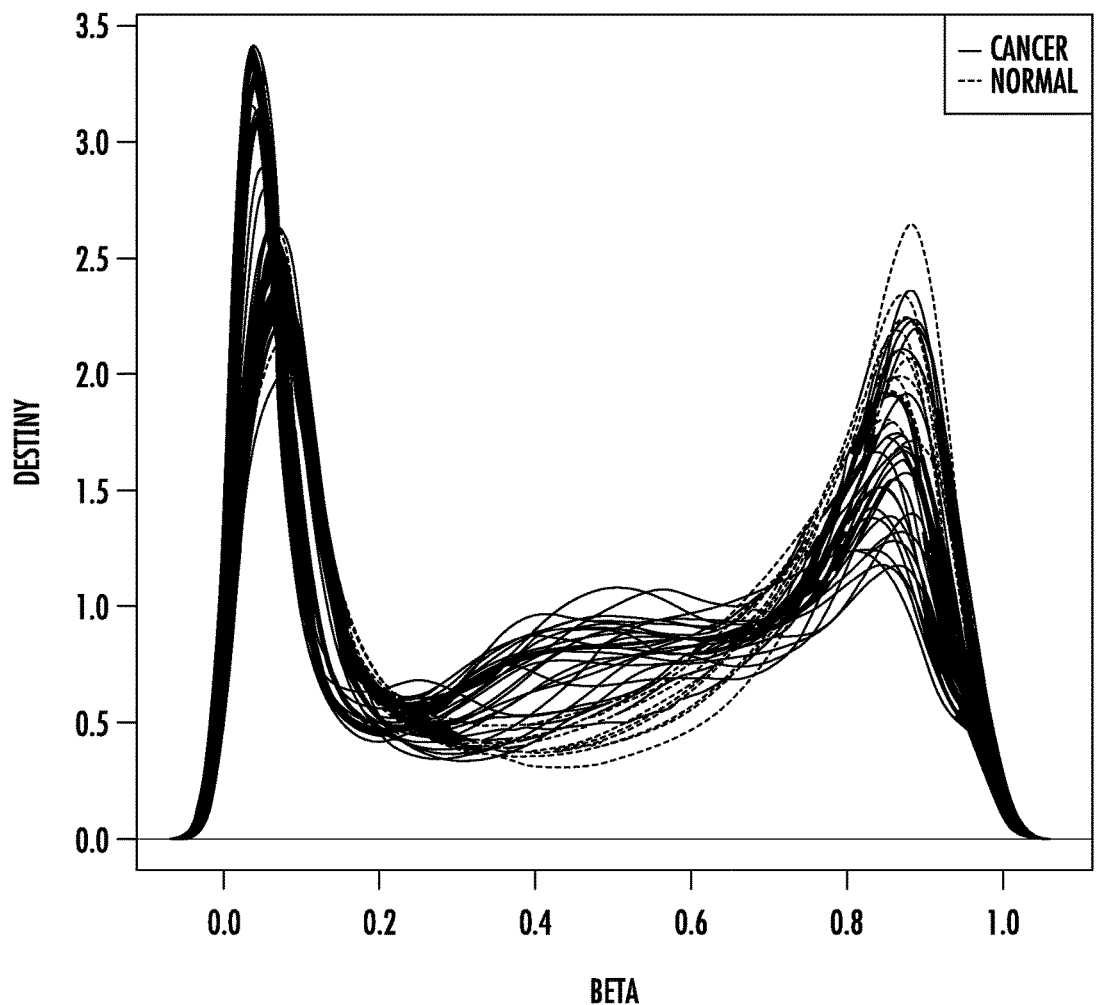
FIG. 1c is a density plot of HNSCC and UPPP 450K beta values across the genome.
Figure 2A:
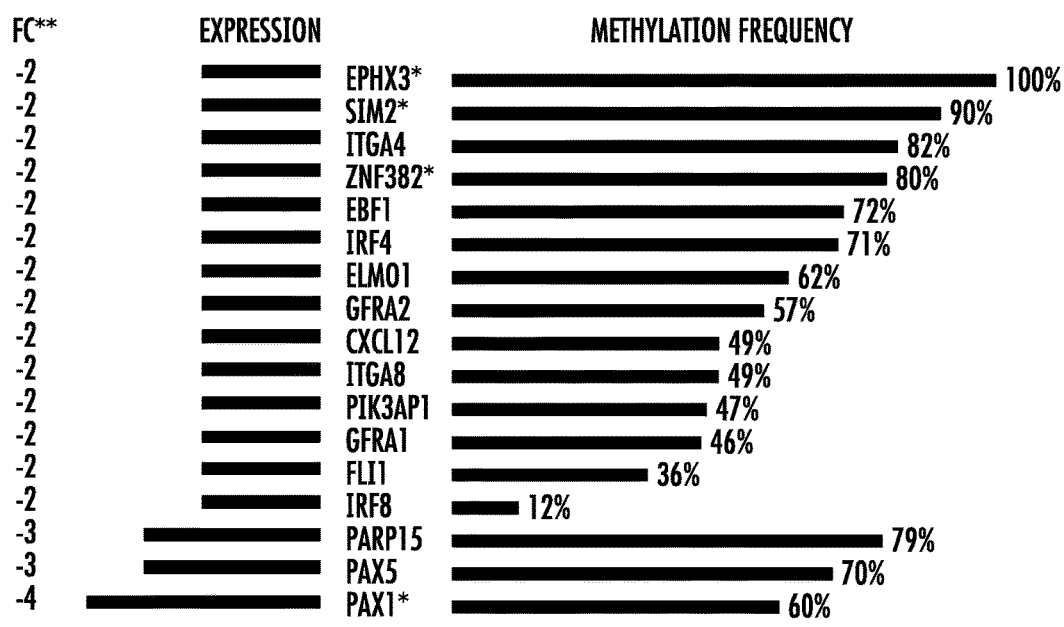
FIG. 2a shows integrative analysis of co-localized promoter methylation and somatic mutations with concurrent expression changes. Here is a graphic representation of methylated genes with fold change differences in expression greater than 2.
Figure 2B:
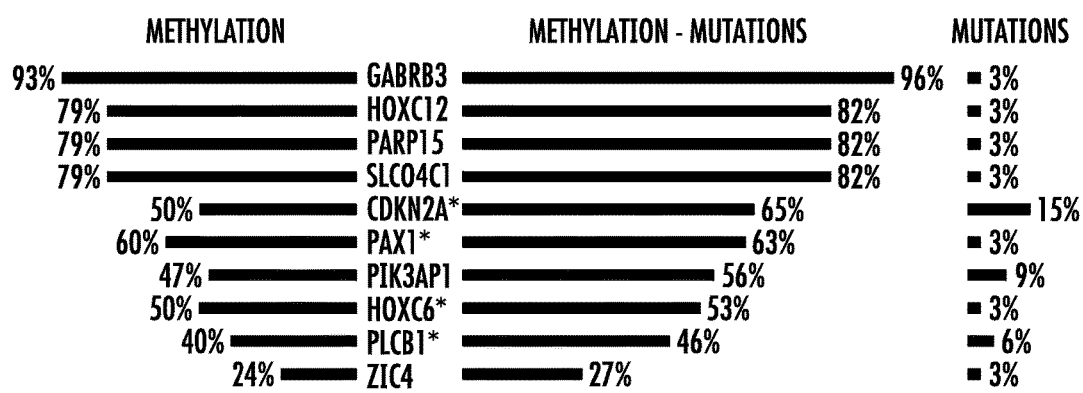
FIG. 2b is a graph showing genes with co-localized promoter methylation and somatic mutations in HNSCC.

Integration of greater promoter methylation and somatic mutation profiles. To validate the MBD-seq results we evaluated genome-wide differential methylation with the Human Methylation 450K Beadchip in 41 cancer and 16 UPPP samples (FIG. 1c). The intersection of unbiased genome-wide methylation sequencing and methylation array screens uncovered 316 genes, which undergo promoter methylation in HNSCC. We found close to 60% concordance between concurrent greater promoter methylation and gene downregulation, with PAX1 and PAX5 exhibiting the greatest expression loss (FIG. 2a). We subsequently intersected the greater promoter methylome with the mutational landscape of HNSCC (1) and identified concurrent promoter methylation and somatic mutations in ten tumor suppressor genes (FIG. 2b). To determine the extent of correlation between differential methylation and mRNA expression patterns, we carried out mRNA expression microarray analysis (Affymetrix Gene ST 2.0).

Example 3

Gene Set Enrichment and Risk Factors Analyses. Unbiased genome-wide analyses were performed to visualize and interpret the large amount of data produced by the sequencing and microarray experiments. Unsupervised hierarchical clustering of the differential methylation events in HNSCC revealed an evident acquisition of stemness-like genome-wide loss of methylation associated to chromosomal instability, together with promoter specific gains in methylation (data not shown). Analysis of Functional Annotation (AFA) was then used to integrate the HNSCC methylation, mutation, and expression landscapes and detect alterations in cellular signaling pathways, protein-protein interaction networks (14), and gene ontology (GO) in HNSCC. AFA revealed that pathways involved in development, differentiation, adhesion, proliferation, and biological/cellular/transcriptional regulation are impacted by concurrent promoter methylation, mutations, and differential gene expression in HNSCC (data not shown). AFA also showed that pathways involved in immune system development, and cell differentiation, proliferation, growth and renewal are impacted by concurrent epigenetic and genetic alterations in HNSCC (data not shown).

Figure 2C:
FIG. 2c depicts the etiologic factors associated with promoter methylation and somatic mutations.

MBD-seq analysis discovered a link between greater promoter methylation and etiologic factors. PAX1 was methylated in all HPV negative tumors whereas zero methylation events of this gene were observed in HPV positive tumors. PAX1 was also methylated in most patients with a history of tobacco exposure (71%), while only 33% of patients without tobacco exposure history exhibited PAX1 methylation. Most HPV negative tumors (83%) showed PAX5 methylation compared to 25% of HPV positive tumors. On the contrary, tumors from patients with a history of tobacco exposure (57%) had similar frequency of PAX5 methylation to patients with no smoking history (67%). We also observed concurrent genomic and epigenomic associations with viral and tobacco exposures. Patients with TP53 mutations also had PAX1 promoter methylation, history of tobacco exposure and were HPV negative. Most (83%) of the patients with TP53 mutations had evidence of PAX5 methylation (FIG. 2c).

Example 4

Figure 6:
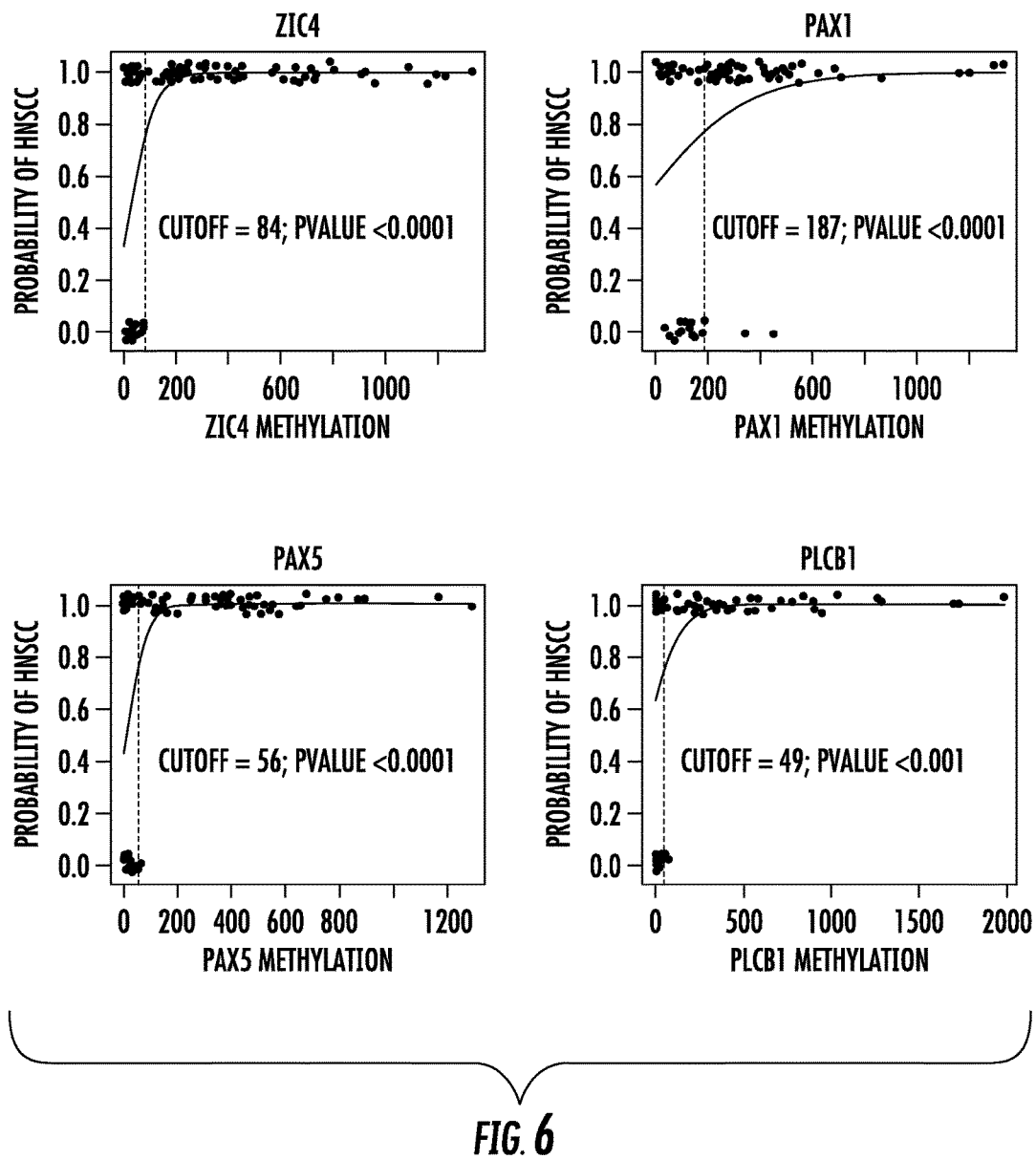
FIG. 6 depicts Q-MSP results for PAX1, PAX5, ZIC4 and PLCB1. The graph is an expression of the logistic regression, Pr (HNSCC=1)=logit$^{-1}$ ($b_0$+$b_1$×methylation) in tissue from 76 participants with data overlain. The predictor methylation is the QMSP value for each case (1) and each control (0). Cutoff methylation values for PAX1, PAX5 ZIC4 and PLCB1 are shown by the vertical dotted line. Probability of HNSCC is shown in darkest gray.
Figure 7:
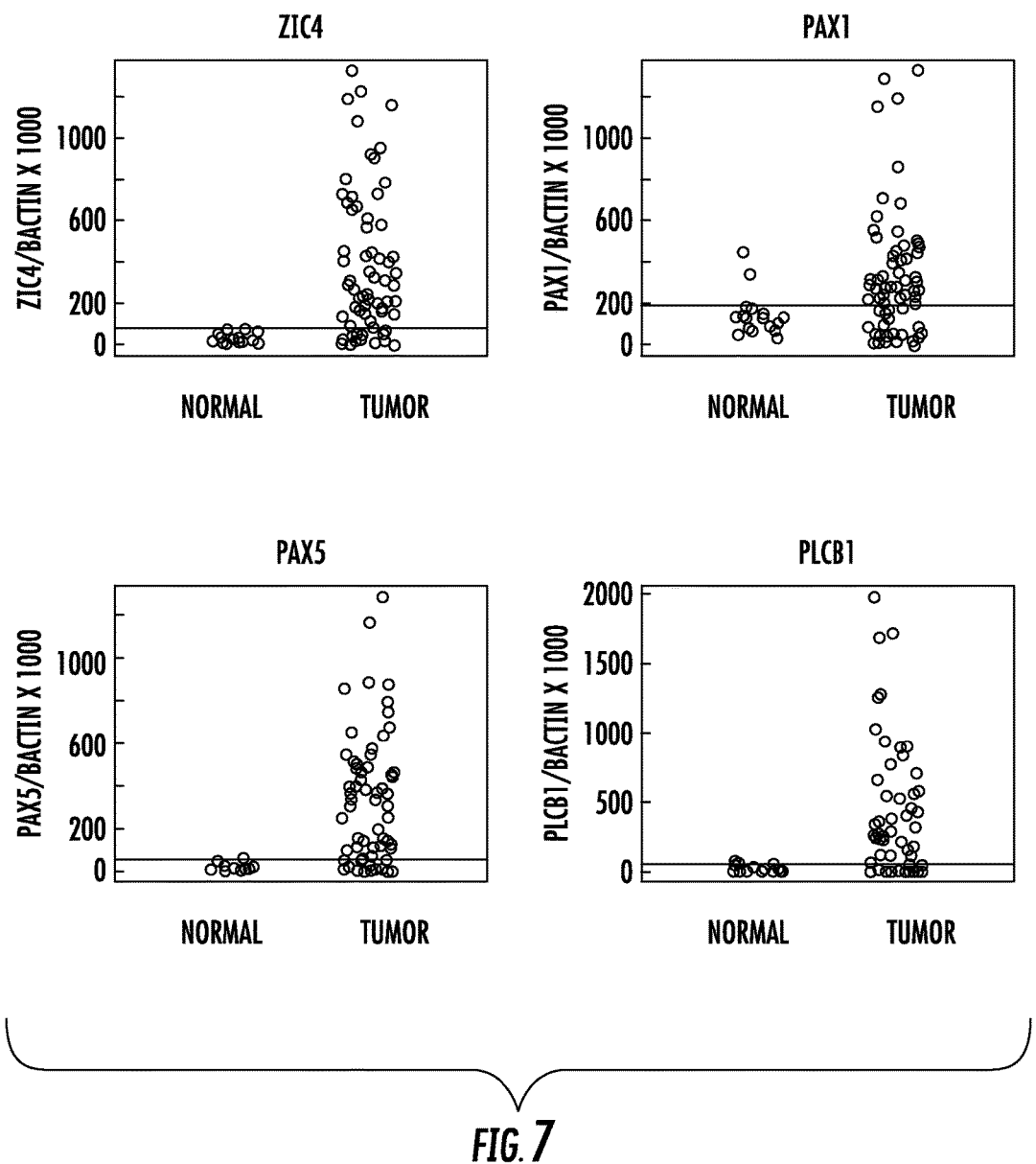
FIG. 7 shows scatterplots of quantitative MSP analysis of candidate genes promoters in the validation screen cohort, which consisted of 76 HNSCC tumor tissue samples and 19 normal tissue samples obtained from uvulopharyngopalatoplasty (UPPP) procedures performed in non-cancer patients. The relative level of methylated DNA for each gene in each sample was determined as a ratio of MSP for the amplified gene to ACTB and then multiplied by 1000 [(average value of duplicates of gene of interest/average value of duplicates of ACTB)×1000] for, PAX1, PAX5, ZIC4 and PLCB1. The line denotes cutoff value.
Figure 8:
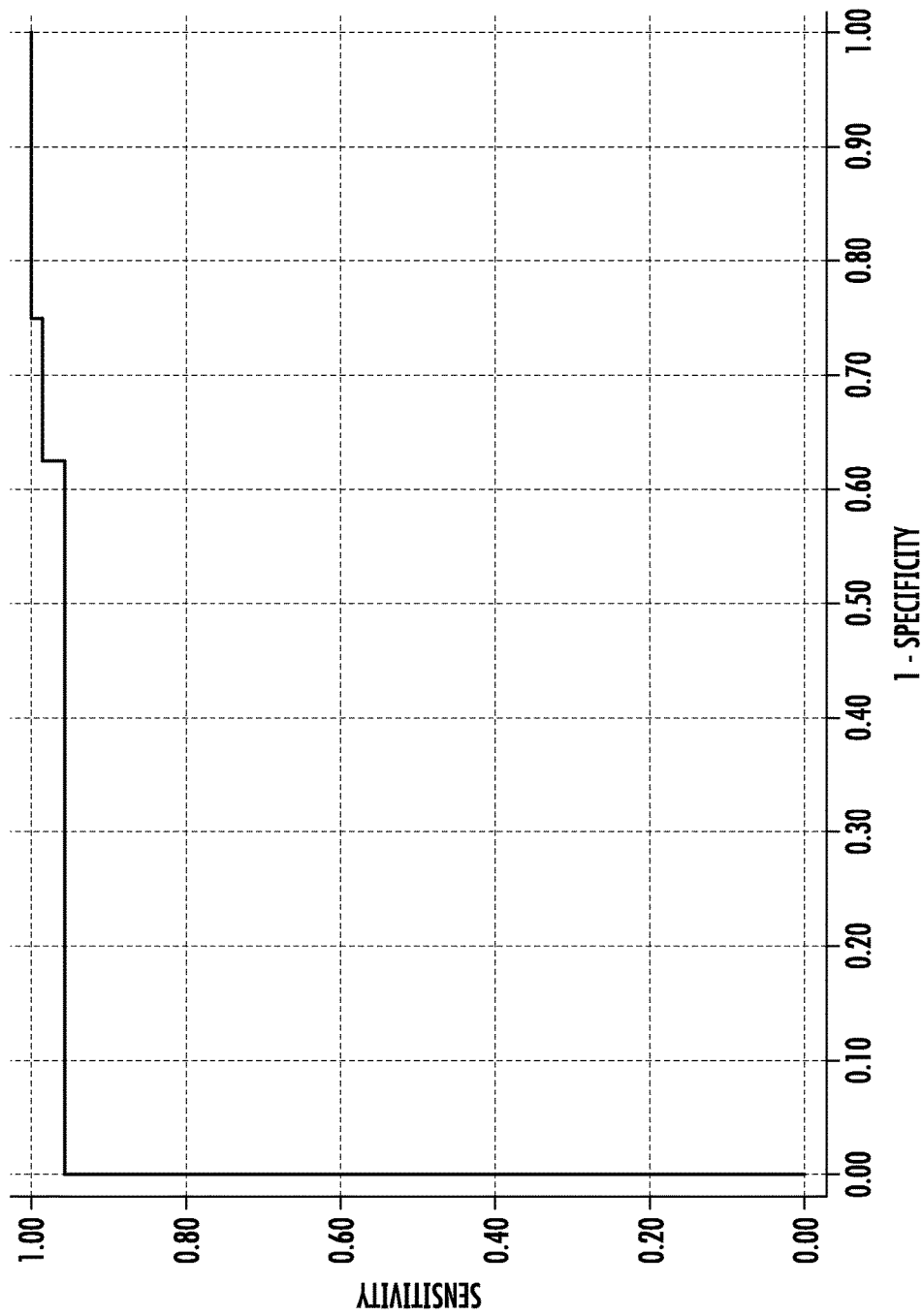
FIG. 8 depicts the Receiver Operator Characteristics (ROC) curve for promoter methylation of PAX1, PAX5, ZIC4 and PLCB1 genes in the validation cohort. The figure shows that for this four gene panel the qMSP results have 96% sensitivity, 94% specificity, a 0.97 AUC and a Positive Predictive Value of 98.5%.

Validation with quantitative methylation specific PCR and TCGA data. To further validate our findings, we performed quantitative methylation specific PCR (qMSP) in 76 cancer and 19 UPPP cases. We found that PAX1 ($p<0.0001$), PAX5 ($p<0.0001$), ZIC4 ($p<0.0001$), and PLCB1 ($p<0.001$) methylation distinguished tumor from UPPP samples. (FIGS. 6-7). PAX1 had 68% sensitivity, 90% specificity and a 0.72 AUC; PAX5 had 80% sensitivity, 94% specificity and a 0.86 AUC; ZIC4 had 73% sensitivity, 100% specificity and a 0.87 AUC; PLCB1 had 55% sensitivity, 84% specificity and a 0.70 AUC. A gene panel combining promoter methylation results for these four genes had 96% sensitivity, 94% specificity, a 0.97 AUC and a Positive Predictive Value of 98.5% (FIG. 8). Methylation frequencies for PAX1, PAX5, ZIC4 and PLCB1 in tumor samples were 68.3%, 78.6%, 75.9% and 52.4%, respectively (table 4). Chi-square test revealed an association between methylation in PLCB1 and tumor site, $p<0.01$. Tumors of the oral cavity and oropharynx were the most frequently methylated.

TABLE 4

Sensitivity, Specificity and AUC results for qMSP analysis

| Gene | AUC | Sensitivity | Specificity | qMSP cutoff | Correctly classified | Methylation frequency |
|------|-----|-------------|-------------|-------------|----------------------|-----------------------|
| PAX 5 | 0.86 | 80 | 94 | 55.8 | 82.40% | 0.786 |
| ZIC4 | 0.87 | 75 | 100 | 83.7 | 80.4% | 0.795 |
| PAX1 | 0.72 | 68 | 90 | 186.4 | 72.3% | 0.683 |
| PLCB1 | 0.7 | 55 | 84 | 49 | 60.4% | 0.523 |

All samples harboring CDKN2A mutations had PAX1 methylation (p<0.0001) as most of TP53 mutated samples (p<0.01). More than half of NOTCH1 (61.5%, p<0.0001) mutated samples also exhibited PAX1 promoter methylation. All the samples with mutations in FBXW7 (p<0.0001), and most of the samples with mutations in TP53 (79%, p<0.0001), and NOTCH1 (92%, p<0.0001) were methylated in the PAX5 promoter.

We corroborated our qMSP results by analyzing The Cancer Genome Atlas (TCGA) publicly available data from 279 HNSCC patients (tcga-data.nci.nih.gov). PAX5 promoter methylation was associated with TP53 mutations (p=0.02), while PAX1 promoter methylation was associated with NOTCH1 mutations (p<0.0001). This evidence suggests a frequent occurrence of previously unreported interactions between PAX1 and PAX5 promoter methylation and exonic mutations in NOTCH1 and TP53 in HNSCC (data not shown). The Kaplan-Meier curves (FIG. 9) show the following: 1) patients with PAX5 promoter methylation had a worse outcome than those without (p=0.001); 2) five year survival outcomes were 2.5 times worse for African Americans with a PAX5 methylation than Non-Latino Whites with PAX5 methylation. (p=0.01); 3) TCGA patients with PAX5 promoter methylation had a worse outcome than those without it (p=0.02); and TCGA patients of all races with combined PAX5 promoter methylation and TP53 mutations had a worse overall survival than patients with TP53 mutations alone (p=0.001).

Figure 10:
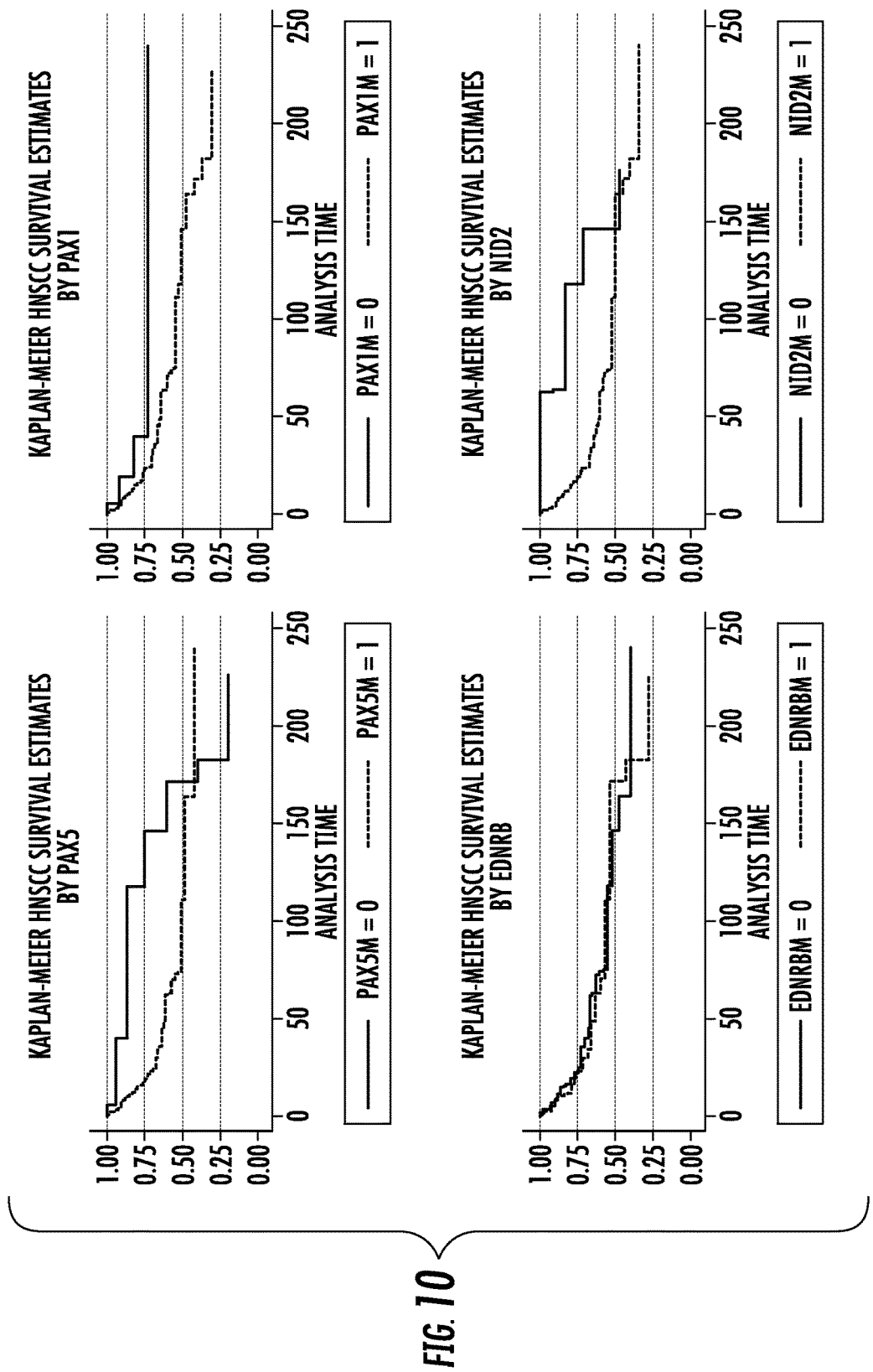
FIG. 10 is a series of Kaplan-Meier curves depicting the difference in survival of patients having promoter methylation of the PAX5, PAX1, EDNRB and NID2 genes. Both PAX5 and NID2 promoter methylation was significantly associated with poorer survival outcomes compared to controls.

Furthermore, patients having promoter methylation of either PAX5 or NID2 had significantly poorer survival outcomes, while methylation of PAX1 and EDNRB promoters were not significantly different from controls (FIG. 10).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES AND NOTES

1. N. Agrawal et al., Exome sequencing of head and neck squamous cell carcinoma reveals inactivating mutations in NOTCH1. *Science* 333, 1154 (Aug. 26, 2011).
2. N. Stransky et al., The mutational landscape of head and neck squamous cell carcinoma. *Science* 333, 1157 (Aug. 26, 2011).
3. M. L. Poeta et al., TP53 mutations and survival in squamous-cell carcinoma of the head and neck. *N Engl J Med* 357, 2552 (Dec. 20, 2007).
4. K. K. Ang et al., Human papillomavirus and survival of patients with oropharyngeal cancer. *N Engl J Med* 363, 24 (Jul. 1, 2010).
5. R. Guerrero-Preston et al., NID2 and HOXA9 promoter hypermethylation as biomarkers for prevention and early detection in oral cavity squamous cell carcinoma tissues and saliva. *Cancer prevention research* 4, 1061 (July, 2011).
6. A. L. Carvalho et al., Deleted in colorectal cancer is a putative conditional tumorsuppressor gene inactivated by promoter hypermethylation in head and neck squamous cell carcinoma. *Cancer Res* 66, 9401 (Oct. 1, 2006).
7. S. Demokan et al., KIF1A and EDNRB are differentially methylated in primary HNSCC and salivary rinses. *Int J Cancer* 127, 2351 (Nov. 15, 2010).
8. C. R. Leemans, B. J. Braakhuis, R. H. Brakenhoff, The molecular biology of head and neck cancer. *Nature reviews. Cancer* 11, 9 (January, 2011).
9. L. G. Morris et al., Recurrent somatic mutation of FAT1 in multiple human cancers leads to aberrant Wnt activation. *Nat Genet* 45, 253 (March, 2013).
10. J. R. Berenson, J. Yang, R. A. Mickel, Frequent amplification of the bcl-1 locus in head and neck squamous cell carcinomas. *Oncogene* 4, 1111 (September, 1989).
11. D. Serre, B. H. Lee, A. H. Ting, MBD-isolated Genome Sequencing provides a high-throughput and comprehensive survey of DNA methylation in the human genome. *Nucleic acids research* 38, 391 (January, 2010).
12. J. Feng, T. Liu, Y. Zhang, Using MACS to identify peaks from ChIP-Seq data. *Current protocols in bioinformatics/editoral board*, Andreas D. Baxevanis . . . [et al.] Chapter 2, Unit 2 14 (June, 2011).
13. A. E. Jaffe et al., Bump hunting to identify differentially methylated regions in epigenetic epidemiology studies. *International journal of epidemiology* 41, 200 (February, 2012).

14. R. Lister et al., Human DNA methylomes at base resolution show widespread epigenomic differences. *Nature* 462, 315 (Nov. 19, 2009).
15. S. Mani et al., DNA methylation changes associated with risk factors in tumors of the upper aerodigestive tract. *Epigenetics: official journal of the DNA Methylation Society* 7, 270 (March, 2012).
16. B. Turkbey et al., Prostate Cancer: Can Multiparametric MR Imaging Help Identify Patients Who Are Candidates for Active Surveillance? *Radiology*, (Mar. 6, 2013).
17. B. Turkbey et al., Correlation of magnetic resonance imaging tumor volume with histopathology. *The Journal of urology* 188, 1157 (October, 2012).
18. V. Shah et al., Decision support system for localizing prostate cancer based on multiparametric magnetic resonance imaging. *Med Phys* 39, 4093 (July, 2012).
19. R. A. Irizarry et al., The human colon cancer methylome shows similar hypo- and hypermethylation at conserved tissue-specific CpG island shores. *Nat Genet* 41, 178 (February, 2009).
20. E. Mena et al., 11C-Acetate PET/CT in localized prostate cancer: a study with MRI and histopathologic correlation. *Journal of nuclear medicine: official publication, Society of Nuclear Medicine* 53, 538 (April, 2012).
21. E. T. Stuart, R. Haffner, M. Oren, P. Gruss, Loss of p53 function through PAX mediated transcriptional repression. *EMBO J* 14, 5638 (Nov. 15, 1995).
22. P. O'Brien, P. Morin, Jr., R. J. Ouellette, G. A. Robichaud, The Pax-5 gene: a pluripotent regulator of B-cell differentiation and cancer disease. *Cancer Res* 71, 7345 (Dec. 15, 2011).
23. C. B. Moelans, A. H. Verschuur-Maes, P. J. van Diest, Frequent promoter hypermethylation of BRCA2, CDH13, MSH6, PAX5, PAX6 and WT1 in ductal carcinoma in situ and invasive breast cancer. *J Pathol* 225, 222 (October, 2011).
24. E. Torlakovic et al., Pax-5 expression in nonhematopoietic tissues. *Am J Clin Pathol* 126, 798 (November, 2006).
25. W. Liu et al., Paired box gene 5 is a novel tumor suppressor in hepatocellular carcinoma through interaction with p53 signaling pathway. *Hepatology* 53, 843 (March, 2011).
26. X. Li et al., Epigenetic inactivation of paired box gene 5, a novel tumor suppressor gene, through direct upregulation of p53 is associated with prognosis in gastric cancer patients. *Oncogene* 31, 3419 (Jul. 19, 2012).
27. K. P. Nera et al., Loss of Pax5 promotes plasma cell differentiation. *Immunity* 24, 283 (March, 2006).
28. C. Cobaleda, A. Schebesta, A. Delogu, M. Busslinger, Pax5: the guardian of B cell identity and function. *Nat Immunol* 8, 463 (May, 2007).
29. V. Bolos, J. Grego-Bessa, J. L. de la Pompa, Notch signaling in development and cancer. *Endocr Rev* 28, 339 (May, 2007).
30. A. Sengupta et al., Deregulation and cross talk among Sonic hedgehog, Wnt, Hox and Notch signaling in chronic myeloid leukemia progression. *Leukemia* 21, 949 (May, 2007).
31. D. S. Wall et al., Progenitor cell proliferation in the retina is dependent on Notch independent Sonic hedgehog/Hes1 activity. *J Cell Biol* 184, 101 (Jan. 12, 2009).
32. L. Landsman, A. Parent, M. Hebrok, Elevated Hedgehog/Gli signaling causes beta-cell dedifferentiation in mice. *Proc Natl Acad Sci USA* 108, 17010 (Oct. 11, 2011).
33. A. Forastiere, W. Koch, A. Trotti, D. Sidransky, Head and neck cancer. *N Engl J Med* 345, 1890 (Dec. 27, 2001).
34. C. Cillo, M. Cantile, A. Faiella, E. Boncinelli, Homeobox genes in normal and malignant cells. *J Cell Physiol* 188, 161 (August, 2001).
35. M. Schubert et al., Retinoic acid signaling acts via Hox1 to establish the posterior limit of the pharynx in the chordate amphioxus. *Development* 132, 61 (January, 2005).
36. D. Koop et al., Retinoic acid signaling targets Hox genes during the amphioxus gastrula stage: insights into early anterior-posterior patterning of the chordate body plan. *Dev Biol* 338, 98 (Feb. 1, 2010).
37. W. M. Koch et al., p53 mutation and locoregional treatment failure in head and neck squamous cell carcinoma. *Journal of the National Cancer Institute* 88, 1580 (Nov. 6, 1996).
38. R. A. Harris et al., Comparison of sequencing-based methods to profile DNA methylation and identification of monoallelic epigenetic modifications. *Nature biotechnology* 28, 1097 (October, 2010).
39. C. Bock et al., Quantitative comparison of genome-wide DNA methylation mapping technologies. *Nature biotechnology* 28, 1106 (October, 2010).
40. S. Yegnasubramanian et al., Chromosome-wide mapping of DNA methylation patterns in normal and malignant prostate cells reveals pervasive methylation of gene-associated and conserved intergenic sequences. *BMC genomics* 12, 313 (2011).
41. Y. Zhang et al., Model-based analysis of ChIP-Seq (MACS). *Genome Biol* 9, R137 (2008).
42. J. Feng, T. Liu, B. Qin, Y. Zhang, X. S. Liu, Identifying ChIP-seq enrichment using MACS. *Nature protocols* 7, 1728 (September, 2012).
43. R. Jaenisch, A. Bird, Epigenetic regulation of gene expression: how the genome integrates intrinsic and environmental signals. *Nat Genet* 33 Suppl, 245 (March, 2003).
44. K. D. Hansen et al., Increased methylation variation in epigenetic domains across cancer types. *Nat Genet* 43, 768 (August, 2011).
45. J. T. Leek, W. E. Johnson, H. S. Parker, A. E. Jaffe, J. D. Storey, The sva package for removing batch effects and other unwanted variation in high throughput experiments. *Bioinformatics* 28, 882 (Mar. 15, 2012).
46. F. Marabita et al., An evaluation of analysis pipelines for DNA methylation profiling using the Illumina HumanMethylation450 BeadChip platform. *Epigenetics: official journal of the DNA Methylation Society* 8, 333 (Mar. 1, 2013).
47. K. D. A. Hansen, M. (2013).
48. R. A. A. Irizarry, M.; Corrada Bravo, H.; Hansen, K. D.; Jaffee, H. A. (2013).
49. S. Y. Kim, D. J. Volsky, PAGE: parametric analysis of gene set enrichment. *BMC bioinformatics* 6, 144 (2005).
50. S. Tyekucheva, L. Marchionni, R. Karchin, G. Parmigiani, Integrating diverse genomic data using gene sets. *Genome Biol* 12, R105 (2011).
51. Y. Benjamini, D. Drai, G. Elmer, N. Kafkafi, I. Golani, Controlling the false discovery rate in behavior genetics research. *Behavioural brain research* 125, 279 (Nov. 1, 2001).
52. V. K. Mootha et al., Identification of a gene causing human cytochrome c oxidase deficiency by integrative genomics. *Proc Natl Acad Sci USA* 100, 605 (Jan. 21, 2003).

53. A. Subramanian et al., Gene set enrichment analysis: a knowledge-based approach for interpreting genome-wide expression profiles. *Proc Natl Acad Sci USA* 102, 15545 (Oct. 25, 2005).
54. E. M. Schaeffer et al., Androgen-induced programs for prostate epithelial growth and invasion arise in embryogenesis and are reactivated in cancer. *Oncogene* 27, 7180 (Dec. 4, 2008).
55. V. C. Daniel et al., A primary xenograft model of small-cell lung cancer reveals irreversible changes in gene expression imposed by culture in vitro. *Cancer Res* 69, 3364 (Apr. 15, 2009).
56. A. E. Ross et al., Gene expression pathways of high grade localized prostate cancer. *Prostate*, (Feb. 25, 2011).
57. B. Benassi et al., MYC is activated by USP2a-mediated modulation of microRNAs in prostate cancer. *Cancer Discov* 2, 236 (March, 2012).
58. H. Liu, Y. Kim, S. Sharkis, L. Marchionni, Y. Y. Jang, In vivo liver regeneration potential of human induced pluripotent stem cells from diverse origins. *Sci Transl Med* 3, 82ra39 (May 11, 2011).
59. M. O. Hoque et al., Quantitation of promoter methylation of multiple genes in urine DNA and bladder cancer detection. *Journal of the National Cancer Institute* 98, 996 (Jul. 19, 2006).
60. A. Lagergren, C. Manetopoulos, H. Axelson, M. Sigvardsson, Neuroblastoma and pre-B lymphoma cells share expression of key transcription factors but display tissue restricted target gene expression. *BMC Cancer* 4, 80 (Nov. 15, 2004).
61. C. G. Mullighan et al., Genome-wide analysis of genetic alterations in acute lymphoblastic leukaemia. *Nature* 446, 758 (Apr. 12, 2007).
62. R. L. Riley, E. Van der Put, A. M. King, D. Frasca, B. B. Blomberg, Deficient B lymphopoiesis in murine senescence: potential roles for dysregulation of E2A, Pax-5, and STAT5. *Semin Immunol* 17, 330 (October, 2005).
63. Z. Chen et al., Transcription factors E2A, FOXO1 and FOXP1 regulate recombination activating gene expression in cancer cells. *PLoS One* 6, e20475 (2011).
64. W. A. Palmisano et al., Aberrant promoter methylation of the transcription factor genes PAX5 alpha and beta in human cancers. *Cancer Res* 63, 4620 (Aug. 1, 2003).
65. E. M. Mandel, R. Grosschedl, Transcription control of early B cell differentiation. *Curr Opin Immunol* 22, 161 (April, 2010).
66. D. J. Todd, A. H. Lee, L. H. Glimcher, The endoplasmic reticulum stress response in immunity and autoimmunity. *Nat Rev Immunol* 8, 663 (September, 2008).
67. J. Aubin, M. Lemieux, J. Moreau, J. Lapointe, L. Jeannotte, Cooperation of Hoxa5 and Pax1 genes during formation of the pectoral girdle. *Dev Biol* 244, 96 (Apr. 1, 2002).
68. C. Mammucari et al., Integration of Notch1 and calcineurin/NFAT signaling pathways in keratinocyte growth and differentiation control. *Dev Cell* 8, 665 (May, 2005).
69. N. R. Manley, M. R. Capecchi, The role of Hoxa-3 in mouse thymus and thyroid development. *Development* 121, 1989 (July, 1995).
70. L. Sang, J. M. Roberts, H. A. Coller, Hijacking HES1: how tumors co-opt the antidifferentiation strategies of quiescent cells. *Trends Mol Med* 16, 17 (January, 2010).
71. P. Mill et al., Sonic hedgehog-dependent activation of Gli2 is essential for embryonic hair follicle development. *Genes Dev* 17, 282 (Jan. 15, 2003).
72. L. Buttitta, R. Mo, C. C. Hui, C. M. Fan, Interplays of Gli2 and Gli3 and their requirement in mediating Shh-dependent sclerotome induction. *Development* 130, 6233 (December, 2003).
73. I. Rodrigo, R. E. Hill, R. Balling, A. Munsterberg, K. Imai, Pax1 and Pax9 activate Bapx1 to induce chondrogenic differentiation in the sclerotome. *Development* 130, 473 (February, 2003).

---

The invention claimed is:

1. A method for identifying an increased risk for a poor survival outcome in a subject having head and neck squamous cell cancer comprising:
   a) obtaining nucleic acid from a test sample from the subject, wherein the test sample is from a specimen selected from the group consisting of a tissue specimen, a biopsy specimen, a surgical specimen, saliva, and a cytological specimen;
   b) performing bisulfite modification to the nucleic acid in a);
   c) performing quantitative methylation specific PCR (QMSP) on bisulfite modified nucleic acid from b) using PCR primers and probes specific for the promoter region of one or more genes of interest, wherein the one or more genes of interest are selected from the group consisting of PAX1, PAX5, ZIC4, and PLCB1, and the primers and probes are selected from the group consisting of SEQ ID NOS: 4-15;
   d) determining the promoter methylation level of the promoter regions of the one or more genes of interest in the nucleic acid from the test sample of the subject;
   e) providing a reference non-neoplastic sample, wherein the reference non-neoplastic sample is from a specimen selected from the group consisting of a tissue specimen, a biopsy specimen, a surgical specimen, saliva, and a cytological specimen;
   f) comparing the level of promoter methylation of the one or more genes of interest from the test sample of the subject, to the level of promoter methylation of the one or more genes of interest in a reference non-neoplastic sample;
   g) identifying an increased risk of poor survival outcome for the subject having head and neck squamous cell cancer when the level of promoter methylation of the one or more genes of interest in the test sample of the subject, is increased relative to the level of promoter methylation of the one or more genes of interest in the reference non-neoplastic test indicating epigenetic silencing of the one or more genes of interest; and
   h) adjusting or modifying the planned treatment of the subject as a result of the increased risk of poor survival in the subject having head and neck squamous cell cancer.

2. The method of claim 1 wherein the test sample contains oral squamous cells or nucleic acids from oral squamous cells.

3. The method of claim 2, wherein the methylation of at least two genes is detected.

4. The method of claim 2, wherein the methylation of at least three genes is detected.

5. The method of claim 2, wherein the methylation of all four genes is detected.

6. The method of claim 1, wherein the methylation of at least PAX5 is determined.

* * * * *